US007923231B2

(12) United States Patent
Brazeau et al.

(10) Patent No.: US 7,923,231 B2
(45) Date of Patent: Apr. 12, 2011

(54) PRODUCTION OF GLUCURONIC ACID USING MYO-INOSITOL OXYGENASE FROM CRYPTOCOCCUS NEOFORMANS

(75) Inventors: Brian Brazeau, St. Paul, MN (US); Jean-Claude De Troostembergh, Tielt-Winge (BE); Paula M. Hicks, Eden Prairie, MN (US); Holly Jessen, Chanhassen, MN (US); Sara C. McFarlan, St. Paul, MN (US); Willy Obyn, Kampenhout (BE); Fernando A. Sanchez-Riera, Eden Prairie, MN (US); William A. Schroeder, Brooklyn Park, MN (US)

(73) Assignee: Cargill, Incorporated, Wayzata, MN (US)

( * ) Notice: Subject to any disclaimer, the term of this patent is extended or adjusted under 35 U.S.C. 154(b) by 1326 days.

(21) Appl. No.: 11/015,563

(22) Filed: Dec. 17, 2004

(65) Prior Publication Data

US 2006/0134742 A1    Jun. 22, 2006

(51) Int. Cl.
*C12N 1/21*     (2006.01)
*C12N 9/02*     (2006.01)
*C12P 21/06*    (2006.01)

(52) U.S. Cl. .................... 435/189; 435/69.1; 435/252.3; 435/136

(58) Field of Classification Search .................... None
See application file for complete search history.

(56) References Cited

U.S. PATENT DOCUMENTS

| | | | |
|---|---|---|---|
| 2,615,053 A | 10/1952 | Artz et al. | |
| 4,337,202 A * | 6/1982 | Hearon et al. | 549/314 |
| 4,920,048 A | 4/1990 | Diderichsen | |
| 4,952,496 A | 8/1990 | Studier et al. | |
| 5,693,489 A | 12/1997 | Studier et al. | |
| 5,824,528 A | 10/1998 | Studier et al. | |
| 5,830,694 A | 11/1998 | Studier et al. | |
| 5,869,320 A | 2/1999 | Studier et al. | |
| 5,912,361 A | 6/1999 | Tsuchioka et al. | |
| 6,455,284 B1 | 9/2002 | Gokarn et al. | |
| 6,518,419 B1 | 2/2003 | Van Der Lugt et al. | |
| 7,326,549 B2 | 2/2008 | Schroeder et al. | |

FOREIGN PATENT DOCUMENTS

| | | |
|---|---|---|
| DE | 3338689 A1 * | 9/1985 |
| GB | 686 396 | 1/1953 |
| GB | 740 205 | 11/1955 |
| JP | 403164143 A * | 7/1991 |
| JP | 2002-153294 | 5/2002 |
| WO | WO 99/32652 | 7/1999 |
| WO | WO 00/50621 | 8/2000 |
| WO | WO 02/074926 | 9/2002 |
| WO | WO 2004/061098 | 7/2004 |

OTHER PUBLICATIONS

Molina et al., "Inositol Synthesis and Catabolism in Cryptococcus neoformans,"Yeast, 15, 1657-1667 (1999).*

"Ascorbic Acid ICSC: 0379" [online]. IPCS Inchem, [retrieved on Aug. 5, 2004]. Retrieved from the Internet: <URL: www.inchem.rog/documents/icsc/icsc/eics0379.htm>, 3 pages.
"Fed Batch Systems," "Product Formation," Semi-continuous culture, ""Synchronous Culture," Limiting nutrient,"[online]. [retrieved on Jun. 26, 2004]. Retrieved from the Internet: <URL: www.rpi.edu/dept/chem-eng/Biotech-Environ/FERMENT>, 5 pages.
"Material Safety Data Sheet Araboascorbic Acid" [online]. [retrieved on Aug. 5, 2004]. Retrieved from the Internet: URL:www.business_services.oregonstate.edu/property/msds/DATA\2242.htm, 2 pages.
"Myoinositol" [online]. Family Practice Notebook.com, 2004, [retrieved on Jun. 16, 2004]. Retrieved from the Internet: <URL: www.fpnotebook.com/PHA13.htm, 2 pages.
"myo-Inositol" [online]. PDRhealth, [retrieved on Jun. 16, 2004]. Retrieved from the Internet: <URL: www.gettingwell.com/drug_info/nmdrugprofiles/nutsupdrugs/myo_0145.shtml, 4 pages.
"pET-23a-d(+) Vectors," Technical Bulletin TB051, 1998, Novagen, 2 pages.
Arner et al., "*myo*-Inositol oxygenase: molecular cloning and expression of a unique enzyme that oxidizes *myo*-inositol and $_D$-chiro-inositol," *Biochem J.*, 2001, 360(2):313-320.
Arner, "Myo-Inositol Oxygenase: Molecular Enzymology and Tissue Specific Expression," Thesis, 2002, Pennsylvania State University, 123 pages.
Arner et al., "Molecular cloning, expression, and characterization of *myo*-inositol oxygenase from mouse, rat, and human kidney," *Biochem. Biophys. Res. Commun.*, 2004, 324:1386-1392.
Bahar et al., "A Model for the Catabolism of Rhizopine in Rhizobium leguminosarum Involves a Ferredoxin Oxygenase Complex and the Inositol Degradative Pathway," *Molecular Plant-Microbe Interactions*, 1998, 11(11):1057-1068.
Balch et al., "Methanogens: Reevaluation of a Unique Biological Group," *Microbiol. Rev.*, 1979, 43(2):260-296.
Ball, "Studies on Oxidation-Reduction. XXIII. Ascorbic Acid," *J. Biol. Chem.*, 1937, 118:219-239. Bradford, "A Rapid and Sensitive Method for the Quantitation of Microgram Quantities of Protein Utilizing the Principle of Protein-Dye Binding," *Anal. Biochem.*, 1976, 72:248-254.
Broadwater and Fox, "Lactose Fed-Batch Fermentation: A High-Yield Method Suitable for Use with the pET System," *inNovations*, 1995, 1:8-9.
Charalampous and Lyras, "Biochemical Studies on Inositol. IV. Conversion of Inositol to Glucuronic Acid by Rat Kidney Extracts," *J. Biol. Chem.*, 1957, 228(1):1-13.
Charalampous, "Biochemical Studies on Inositol. V. Purification and Properties of the Enzyme that cleaves Inositol to $_D$-Glucuronic Acid," *J. Biol. Chem.* 1959, 234(2):220-227.
Chen et al., "Spectroscopic Studies of Isopenicillin N Synthase. A mononuclear nonheme Fe2+ oxidase with metal coordination sites for small molecules and substrate," *J. Biol. Chem.*, 1989, 264(36):21677-21681.

(Continued)

*Primary Examiner* — Lisa J Hobbs

(57) ABSTRACT

A method is disclosed for increasing the specific activity of myo-inositol oxygenase. The method includes incubating a mixture including myo-inositol oxygenase and a non-sulfur containing reductant under conditions effective to increase the specific activity of the myo-inositol oxygenase. Also disclosed are methods for producing D-glucuronic acid and glucurono-γ-lactone comprising incubating a mixture including myo-inositol, myo-inositol oxygenase, and oxygen under conditions effective to form 5 grams D-glucuronic acid per liter of the mixture to 400 grams D-glucuronic acid per liter of the mixture. Glucurono-γ-lactone can be produced from the D-glucuronic acid product. Also disclosed are organisms and nucleic acids suitable for use in such methods.

26 Claims, 5 Drawing Sheets

OTHER PUBLICATIONS

Chu et al., "Cloning and Expression of the metE Gene in *Escherichia coli*," *Arch. Biochem. Biophys.*, 1985, 239(2):467-474.

Datsenko and Wanner, "One-step inactivation of chromosomal genes in *Escherichia coli* K-12 using PCR products," *Proc. Natl. Acad. Sci. USA*, 2000, 97(12):6640-6645.

Fazldeen and Breitenbach, "A New Sepharose Derivative Containing Covalently Bound *myo*-Inositol: Its Structure and Application," *Monatshefte für Chemie*, 1979, 110:832-830.

Graham and Mantle, "Partial purification of *myo*-inositol oxygenase from ox kidney by using phenyl-Sepharose," *Biochem. Soc. Trans.*, 611th Meeting, Galway, 1985, 13:481.

Hoffman et al., "Lactose Fed-Batch Overexpression of Recombinant Metalloproteins in *Escherichia coli* BL21(DE3): Process Control Yielding High Levels of Metal-Incorporated, Soluble Protein," *Protein Expr. Purif.*, 1995, 6(5):646-654.

Hoffmann, "The Ubiquitous Co-Enzyme UDPGlucuronic Acid. Detoxifying Agent in Kombucha Tea?" [online]. Mar. 24, 2004, [retrieved on May 27, 2004]. Retrieved from the Internet: <URL: www.rpi.edu/dept/chem-eng/Biotech-Enfiron/FERMENT/fedbat.htm, 4 pages.

Hu et al., "Identification of a novel kidney-specific gene downregulated in acute ischemic renal failure," *Am. J. Physiol. Renal Physiol.*, 2000, 279(3):F426-F439.

Kanter et al., "Purification, characterization and functional cloning of inositol oxygenase from *Cryptococcus*," *Yeast*, 2003, 20(16):1317-1329.

Kanter et al., "The inositol oxygenase gene family of *Arabidopsis* is involved in the biosynthesis of nucleotide sugar precursors for cell-wall matrix polysaccharides," *Planta*, 2005, 221(2):243-254.

Kanwar et al., "Relevance of renal-specific oxidoreductase in tubulogenesis during mammalian nephron development," *Am. J. Physiol. Renal Physiol.*, 2002, 282(4):F752-F762.

Koller and Hoffmann-Ostenhof, "*myo*-Inositol Oxygenase from Rat Kidneys. I: Purification by affinity chromatography; physical and catalytic properties," *Hoppe Seyler's Z. Physiol. Chem.*, 1979, 360(4):507-513.

Koller and Koller, "Affinity Chromatography of *myo*-Inositol Oxygenase from Rat Kidney by Means of an Insoluble $_D$-Galacto-Hexodialdose Derivative," *J. Chromatogr.*, 1984, 283:191-197.

Koller and Koller, "*myo*-Inositol Oxygenase From Rat Kidneys. Substrate-dependent oligomerization," *Eur. J. Biochem.*, 1990, 193(2):421-427.

Koller et al., "Myo-inositol oxygenase from oat seedlings," *Mol. Cell. Biochem.*, 1976, 10(1):33-39.

Lee, "High cell-density culture of *Escherichia coli*," *Tibtech*, 1996, 14:98-105.

Lorence et al., "*myo*-Inositol Oxygenase Offers a Possible Entry Point into Plant Ascorbate Biosynthesis," *Plant Physiol.*, 2004, 134:1200-1205.

March et al., "Expression of an Anaplerotic Enzyme, Pyruvate Carboxylase, Improves Recombinant Protein Production in *Escherichia coli*," *Appl. Environ. Microbiol.*, 2002, 68(11):5620-5624.

Menzella et al., "Novel *Escherichia coli* Strain Allows Efficient Recombinant Protein Production Using Lactose as Inducer," *Biotechnology and Bioengineering*, 2003, 82(7):809-817.

Moskala et al., "An Oxygen-18 Tracer Investigation of the Mechanism of myo-Inositol Oxygenase," *Biochem. Biophys. Res. Commun.*, 1981, 99(1):107-113.

Naber et al., "$_L$-*myo*-Inosose-1 as a Probable Intermediate in the Reaction Catalyzed by *myo*-Inositol Oxygenase," *Biochemistry*, 1986, 25(22):7201-7207.

Neubauer et al., "Maximizing the expression of a recombinant gene in *Escherichia coli* by manipulation of induction time using lactose as inducer," *Appl. Microbiol. Biotechnol.*, 1992, 36:739-744.

Novy and Morris, "Use of Glucose to Control Basal Expression in the pET System," *inNovations*, 2003, 13:8-10.

Ou et al., "Stationary phase protein overproduction is a fundamental capability of *Escherichia coli*," *Biochem. Biophys. Res. Commun.*, 2004, 314(1):174-180.

Reddy and Hamilton, "Activation of Homogeneous Preparations of Hog Kidney myo-Inositol oxygenase by Quinolinic Acid and Ferrous Ions," *Biochem. Biophys. Res. Commun.*, 1981, 100(3):1389-1395.

Reddy et al., "*myo*-Inositol Oxygenase from Hog Kidney II. Catalytic Properties of the Homogeneous Enzyme," *J. Biol. Chem.*, 1981, 256(16):8519-8524.

Reddy et al., "*myo*-Inositol Oxygenase from Hog Kidney. I. Purification and characterization of the oxygenase and of an enzyme complex containing the oxygenase and $_D$-glucuronate reductase," *J. Biol. Chem.*, 1981, 256(16):8510-8518.

Ried and Collmer, "An nptI-sacB-sacR cartridge for constructing directed, unmarked mutations in gram-negative bacteria by marker exchange-eviction mutagenesis," *Gene*, 1987, 57(2-3):239-246.

Rocklin et al., "Role of the nonheme Fe(II) center in the biosynthesis of the plant hormone ethylene," *Proc. Natl. Acad. Sci. USA*, 1999, 96(14):7905-7909.

Rosario, "Cryptococcus Neoformans Inositol Catabolic Gene and Protein," Thesis presented to the Department of Biological Sciences, California State University, Long Beach, 1998, pp. 1-70.

Sato et al., "Antioxidant Activity of Synovial Fluid, Hyaluronic Acid, and Two Subcomponents of Hyaluronic Acid," *Arthritis Rheum.*, 1988, 31(1):63-71.

Strandberg et al., "The use of fed batch cultivation for achieving high cell densities in the production of a recombinant protein in *Escherichia coli*," *FEMS Microbiol. Rev.*, 1994, 14:53-56.

Wada et al., "Gene expression and identification of gene therapy targets in diabetic nephropathy," *Kidney Int.*, 2002, 61(Symposium 1):S73-S78.

Williams and Yandell, "Outer-Sphere Electron-Transfer Reactions of Ascorbate Anions," *Aust. J. Chem.*, 1982, 135:1133-1144.

Yang et al., "Identification of a renal-specific oxido-reductase in newborn diabetic mice," *Proc. Natl. Acad. Sci. USA*, 2000, 97(18):9896-9901.

International Search Report mailed Jun. 21, 2008 to International Application No. PCT/US05/45575 filed Dec. 16, 2005.

Enzyme Catalysis in Organic Synthesis, A Comprehensive Handbook, vol. 1, Chapter 4, Enzyme Engineering by directed Evolution, Oliver May et al., (2002).

Biocatalysis in the Pharmaceutical and Biotechnology Industries, Chapter 30, Enzyme Evolution for Chemical Process Applications, Gjalt W. Huisman et al., (2007).

Biocatalysis: giving Nature a helping hand (found at http://www.codexis.com/pdf/Biocatalysis.pdf), (2007).

Engineered Enzymes for Chemical Production, Stephan Luetz et al. Biotechnology and Bioengineering, vol. 101, No. 4, Nov. 1, 2008, pp. 647-653.

\* cited by examiner

**Crystalline
D-Glucurono-γ-Lactone**

PRODUCTION OF GLUCURONIC ACID USING MYO-INOSITOL OXYGENASE FROM CRYPTOCOCCUS NEOFORMANS

TECHNICAL FIELD

This invention relates to the green chemistry production of a health supplement. More particularly, the invention relates to the methods for the production of glucurono-γ-lactone, and compositions useful in such methods.

BACKGROUND

Natural health products and health supplements are becoming increasingly popular. They can be used to help individuals live longer and lead more active lives. D-Glucurono-γ-lactone (also named glucurono-3,6-lactone) ("GGL") is an example of a health supplement that may have positive health benefits. GGL is believed to have a number of positive health effects, including: promoting joint health, providing an anti-inflammatory effect for the skin, lowering abnormally high plasma concentrations of cholesterol or triglycerides, improving bone marrow health, and helping digestion. Additionally, GGL is believed to have synergistic effects with glucosamine or chondroitin sulfate, other popular health supplements.

Currently, GGL is typically produced by a process involving the nitric acid oxidation of starch. This process may use up to 0.5 kg of concentrated nitric acid per kg of GGL produced. Therefore, the nitric acid process has significant associated environmental and safety risks. The production process has a high environmental impact due to the use of the concentrated nitric acid, as well as the waste streams generated by the production process. Additionally, the use of concentrated nitric acid poses significant health and safety issues for workers, often requiring extensive precautionary measures.

There exists a need for a safe, environmentally friendly, and cost-effective method for the production of GGL.

SUMMARY

The invention features methods for increasing the specific activity of myo-inositol oxygenase. In one aspect, a method for increasing the specific activity of myo-inositol oxygenase comprises incubating a mixture including myo-inositol oxygenase and a reductant under conditions effective to increase the specific activity of the myo-inositol oxygenase. The reductant may be a non-sulfur containing reductant. The reductant may be soluble in water. The reductant may include L-ascorbic acid or D-isoascorbic acid. The reductant may lack L-cysteine. In some embodiments, the reductant is present at a concentration from about 1 mM to about 10 mM. In some embodiments, the reductant has a reduction potential greater than about −200 mV, greater than about −100 mV, greater than about 0 mV, or greater than about +25 mV. The reductant can have a reduction potential less than about 500 mV. Myo-inositol oxygenase may be present in a concentration from about 1 mg/ml to about 200 mg/ml. The myo-inositol oxygenase in the incubation mixture may be immobilized. The incubation mixture may include other components, e.g., Fe(II) or a buffer. If included, Fe(II) may be added as ferrous ammonium sulfate, ferrous ascorbate, ferrous sulfate, or ferrous chloride. Fe(II) may be present in a concentration from 0 mM to about 10 mM, or from about 1 mM to about 5 mM. A buffer can be 3-[N-morpholino]propanesulfonic acid or sodium acetate. The buffer may be present at a concentration from 0 mM to about 100 mM. The incubation mixture can comprise a cell lysate, e.g., when myo-inositol oxygenase is added to the mixture as one component of a cell lysate. The cell lysate may be generated by mechanical disruption or chemical disruption. If mechanical disruption is used to form a cell lysate, cells can be cooled to less than 20° C. prior to disruption. Alternatively, the incubation mixture can include whole cells e.g., when myo-inositol oxygenase is added to the mixture as one component of whole cells. Such whole cells can be yeast cells, Gram(+) cells, Gram(−) cells, or filamentous fungi cells. The incubation can occur at a temperature from about −5° C. to about 20° C. The incubation may include incubating the mixture from about 10 minutes to about 360 minutes, or from about 15 minutes to about 150 minutes.

In another aspect, a method for increasing the specific activity of myo-inositol oxygenase includes incubating a mixture comprising myo-inositol oxygenase and Fe(II); and applying a controlled voltage to the mixture under conditions effective to increase the specific activity of the myo-inositol oxygenase.

The invention also features methods for producing D-glucuronic acid. One method for producing D-glucuronic acid includes incubating a mixture including myo-inositol, myo-inositol oxygenase, and oxygen under conditions effective to form D-glucuronic acid. A suitable myo-inositol oxygenase includes a myo-inositol oxygenase from *Phanerochaete chrysosporium*, *Cryptococcus neoformans*, *Cryptococcus lactativorus*, or *Aspergillus nidulans*. Myo-inositol oxygenase can be added to the mixture by a single addition, continuous addition, or periodic addition. Myo-inositol may be present in the mixture at a concentration greater than about 20 grams per liter, greater than about 30 grams per liter, or greater than about 40 grams per liter, but less than about 500 grams per liter. Myo-inositol may be initially present at a concentration greater than 20 grams per liter. Alternatively, myo-inositol may be added periodically or continuously. Oxygen may be present at a concentration greater than about 10 μmol per liter of mixture, or greater than about 140 μmol per liter of mixture. Oxygen may be present at a concentration less than about 6500 μmol per liter of mixture, or less than about 1550 μmol per liter of mixture. Oxygen may be present in the mixture at 10% to 80% saturation. The incubation may occur under a headspace of pure oxygen. The incubation may include sparging air into the mixture, sparging oxygen enriched air into the mixture, or sparging oxygen into the mixture. Oxygen may be present in sufficient quantity to reach an oxygen utilization rate of 20 mmol per liter of mixture per hour. D-glucuronic acid may be present at a concentration from about 5 grams per liter to about 400 grams per liter, e.g., greater than about 10 grams per liter, or greater than about 20 grams per liter. D-glucuronic acid may be present at a concentration less than about 400 grams per liter. The D-glucuronic acid concentration can be greater than the myo-inositol concentration, and can be at least twice the myo-inositol concentration.

In some embodiments, the mixture includes Fe(II). Fe(II) can be present at a concentration of about 0.01 mM to about 40 mM, e.g., 0.01 mM to 20 mM, 0.01 mM to 10 mM, 0.01 mM to 5 mM, or 0.01 mM to 2 mM. In some embodiments, the mixture includes a reductant, for example, L-ascorbic acid or D-isoascorbic acid. The concentration of reductant can be from less than about 10 mM, e.g., 0.01 mM to 10 mM, or 0.01 mM to 5 mM. In another aspect, the mixture may include a buffer. The buffer may be present at a concentration of 0 mM or greater. The buffer may be present at a concentration less than about 20 mM, less than about 10 mM, less than about 5 mM, or less than about 2 mM. In some aspects, no additional may buffer be added to the mixture.

The mixture can also include other components such as a salt, e.g., an inorganic salt or organic salt such as sodium chloride, potassium chloride, or sodium D-glucuronate, at a concentration from about 0.01 M to about 2.0 M, or an antifoam agent. In some embodiments, a base is added to the incubation mixture, for example, sodium hydroxide or potassium hydroxide. The mixture may include cell lysate or whole cells e.g., when myo-inositol oxygenase is added to the mixture as one component of the lysate or cells. The cells may be present in a cell bed. The incubation can occur at a temperature greater than about 0° C., e.g., from about 15° C. to about 50° C., or about 15° C. to about 35° C. In some embodiments, the method also includes clarifying the mixture, demineralizing the mixture, or crystallizing D-glucuronic acid formed during the incubation. In some embodiments, the method also includes clarifying the mixture, crystallizing a salt of D-glucuronic acid, demineralizing the mixture, or crystallizing D-glucuronic acid formed during the incubation. The method may further include forming glucurono-g-lactone from D-glucuronic acid.

The method may further include forming glucurono-γ-lactone from D-glucuronic acid. Forming glucurono-γ-lactone may include clarifying the mixture, demineralizing the mixture, or heating the D-glucuronic acid from the mixture at an acidic pH. Glucurono-γ-lactone can be crystallized after heating the D-glucuronic acid.

Another method of producing D-glucuronic acid includes preincubating a first mixture comprising myo-inositol oxygenase and a reductant under conditions effective to increase the specific activity of myo-inositol oxygenase. A second mixture comprising myo-inositol, the first mixture, and oxygen is then incubated under conditions effective to form D-glucuronic acid. The reductant may be a non-sulfur containing reductant, or the reductant may have a reduction potential greater than about −200 mV. The D-glucuronic acid may be present at a concentration from about 5 to about 400 grams per liter of second mixture.

The invention also features a composition comprising D-glucuronic acid, made by any of the above described processes.

The invention also features methods for producing glucurono-γ-lactone. A method of producing glucurono-γ-lactone includes preincubating a first mixture comprising myo-inositol oxygenase and a reductant under conditions effective to increase the specific activity of myo-inositol oxygenase. A second mixture comprising myo-inositol, the first mixture, and oxygen is then incubated under conditions effective to form D-glucuronic acid. The second mixture is clarified, demineralized, and heated at an acidic pH to result in the formation of glucurono-γ-lactone. The glucurono-γ-lactone thus formed can be crystallized from the acidic solution.

In one aspect, the reductant is a non-sulfur containing reductant. In another aspect, the reductant has a reduction potential greater than about −200 mV. In another aspect, the D-glucuronic acid is present during incubation of the second mixture at a concentration from about 5 to about 400 grams per liter of second mixture.

The invention also features microbial cells having a myo-inositol oxygenase content from about 15% to about 50% by weight total soluble protein. The myo-inositol oxygenase may be a *Phanerochaete chrysosporium* myo-inositol oxygenase, a *Cryptococcus neoformans* myo-inositol oxygenase, a *Cryptococcus lactativorus* myo-inositol oxygenase, or an *Aspergillus nidulans* myo-inositol oxygenase. The cells may include a myo-inositol oxygenase coding sequence operably linked to a T7 promoter, a T7lac promoter, or a T5 promoter.

The cells can be Gram(+) or Gram(−) bacterial cells, e.g., a K-12 strain of *E. coli*. The myo-inositol oxygenase may be integrated into the chromosome of the *E. coli* cells. A transposon may be used to insert a myo-inositol oxygenase gene into the chromosome of the *E. coli* cells. The *E. coli* cells may be metE mutants, relaxed (relA) mutants, recombination deficient (recA) mutants, protease deficient mutants, ompT mutants, lon mutants, clpP mutants, or uxaC mutants. In some embodiments, the cells can metabolize galactose. Transcription of the myo-inositol oxygenase coding sequence may induced by lactose. The invention also features cell lysates. An unpurified cell lysate may have a myo-inositol oxygenase content from about 15% to about 100% by weight total soluble protein, e.g., from about 20% to about 100% by weight total soluble protein.

The invention also features an isolated nucleic acid that comprises a *Cryptococcus neoformans* mio coding sequence that lacks tandem CGA codons for arginine.

The invention also features an isolated plasmid that lacks an antibiotic selectable marker and comprises a *Cryptococcus neoformans* mio coding sequence that lacks tandem CGA codons for arginine, e.g., a plasmid designated pCNAR, present in a bacterial strain having ATCC Accession No. PTA-6449, deposited with the American Type Culture Collection, 10801 University Blvd., Manassas, Va., 20110-2209, on 16 Dec. 2004. The invention also features a Gram-negative bacterial strain having a *Cryptococcus neoformans* mio coding sequence that lacks tandem CGA codons for arginine. The *Cryptococcus neoformans* mio coding sequence may be present on a plasmid. The bacterial strain may be *E. coli* BW30384(DE3)ΔompTΔmetEΔuxaC::pCNAR, having ATCC Accession No. PTA-6449, deposited with the American Type Culture Collection, 10801 University Blvd., Manassas, Va., 20110-2209, on 16 Dec. 2004.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DETAILED DESCRIPTION

I. Definitions

Figure 1:
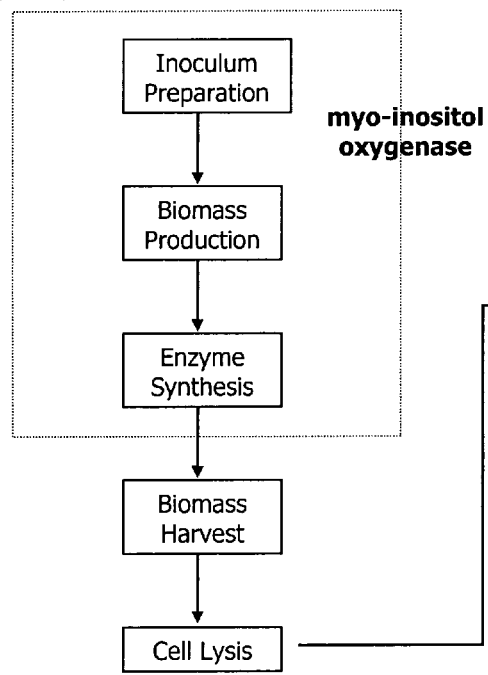
FIG. 1 is a flow diagram showing the production steps of the described process.
Figure 1:
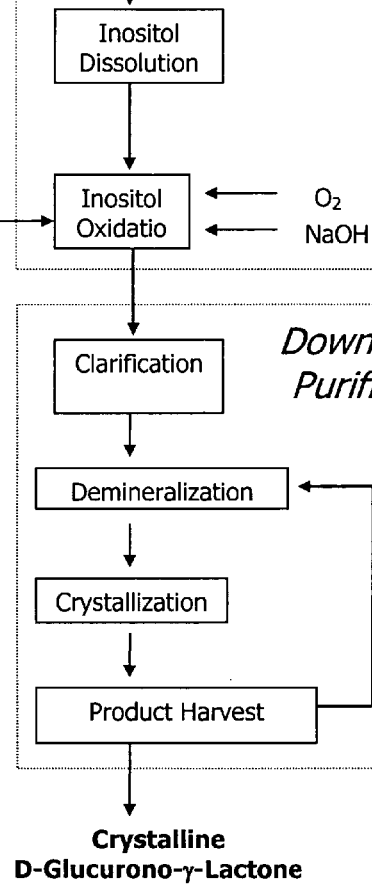

Minimal medium. A medium that contains only inorganic salts, a simple carbon source (such as carbon dioxide or glucose), and water, that supplies minimal or limited nutritional requirements for a particular organism.

Rich medium. A medium that is rich in a wide variety of nutrients, including growth factors, and will support growth for a wide variety of microorganisms. Luria-Bertani broth ("LB"). LB broth contains 10 g/L Bacto Tryptone, 5 g/L Bacto yeast extract, and 10 g/L sodium chloride in water.

Reduction potential. Reduction potential is calculated using the method of Ball, as described in Ball E G, (1937) Studies on Oxidation-Reduction XXIII. Ascorbic Acid, J. Biol. Chem., 118:219-239. The numbers for reduction potential proceed normally, in that a reduction potential of −100 mV is greater than a reduction potential of −200 mV.

Brix degree. A measurement used to correlate density with sugar concentration in a solution. Each degree is equivalent to 1 percent w/v sugar in the solution. In some solutions Brix can be correlated with total solids.

Soluble in water. Soluble in water means that the solubility of the compound equals or exceeds 0.5 grams per liter of water. Examples of soluble compounds include L-ascorbic acid, which has a solubility of 330 grams/liter water, and D-isoascorbic acid which a solubility of 280 grams/liter water.

Organic. As used herein, an organic compound is one that includes carbon and hydrogen, and optionally may include other atoms, such as oxygen, nitrogen, etc.

D-glucuronic acid. The term D-glucuronic acid typically includes the free acid as well as any salts thereof.

L-ascorbic acid. The term L-ascorbic acid typically includes the free acid as well as any salts thereof.

D-isoascorbic acid. The term D-isoascorbic acid typically includes the free acid as well as any salts thereof.

II. Cells Containing a Myo-Inositol Oxygenase Gene

One aspect of the present invention is a cell having increased production of myo-inositol oxygenase ("MIO"). MIO is an Fe(II) containing enzyme that converts myo-inositol to D-glucuronic acid using oxygen, without requiring additional cofactors.

Increasing production of MIO in a cell has enabled a more cost efficient route for the production of GGL. However in most cells, MIO is typically present only at low levels or completely absent. Therefore, in order to increase the production of MIO, MIO may be produced in a genetically engineered cell that has been modified to overexpress a MIO gene. This recombinant host may be a bacterium host cell. Overexpression increases the amount of MIO produced in the cell and results in more MIO per cell mass. Numerous metabolic engineering improvements may be made, for example, in the host cell, in the MIO gene, or in the expression system.

Microbial cells may be modified to increase MIO production, and may contain MIO content from about 15% to about 50% by weight total soluble protein. In other modified cells, MIO content may constitute from about 20% to about 50% by weight total soluble protein, or MIO content may constitute from about 25% to about 50% by weight total soluble protein.

A MIO coding sequence may be obtained from a variety of cell sources. Suitable sources include *Cryptococcus terreus*, *Cryptococcus neoformans*, *Cryptococcus lactativorus*, *Phanerochaete chrysosporium*, and *Aspergillus nidulans*, *Homo sapiens*, *Bos taurus*, *Rattus norvegicus*, *Mus musculus*, *Drosophila melanogaster*, *Arabidopsis thaliana*, *Pinus radiata*, *Zea mays* and *Glycine max*. See, e.g., WO 02/074926. The degeneracy of the genetic code permits codon modification without a corresponding modification of the amino acid sequence. Thus, codons in a MIO nucleic acid can be modified if desired, without modifying the encoded amino acid sequence of the polypeptide, in order to optimize expression in a particular organism. In some embodiments, the amino acid sequence of a MIO polypeptide is modified, in order to optimize expression in a particular organism.

A MIO coding sequence may be fused to sequences encoding N-terminal or C-terminal tags for changing the characteristics of the enzyme. Examples of suitable terminal tags include Maltose Binding Protein, Strep-tag® (IBA, Goettingen, Germany; catalog #2-1345-000), the periplasmic transport signal sequence of pectate lyase B (pelB), Cellulose Binding Domain (CBD), thioredoxin (trxA), disulfide oxidoreductase (dsbA), protein disulfide isomerase (dsbC), and poly-His$_6$. A MIO gene may also be used in the native, non-tagged state.

MIO may also be expressed from a variety of promoters. The amount of MIO produced from a particular promoter can be measured by units of MIO activity produced per mg of total protein or by densitometry analysis of SDS-PAGE. Suitable promoters include T7, T7Lac, and T5, trc, trp, lac and araBAD.

Various host cells may be used for producing MIO. Suitable cells include bacterial cells, yeast cells, and filamentous fungi cells. Bacterial host cells may be used as they are vigorous, tolerant, reproduce rapidly, and can be grown in a variety of cell media. Examples of suitable bacterial host cells include *Escherichia coli* ("*E. coli*"), *Zymomonas* species, *Corynebacterium* species, *Bacillus* species (for example, *B. subtilis*, *B. megaterium* or *B. licheniformis*), *Pseudomonas* species, and *Pantoea* (*Erwinia*) species. Examples of suitable strains of *E. coli* include B strains such as B834(DE3), B834, BL21(DE3), BL21, BL21(DE3)STAR, BL21(DE3)AI, BL21(DE3)pLysS, BLR(DE3), BLR(DE3)pLysS, BLR, Rosetta(DE3), Rosetta, and K-12 strains such as HMS174 (DE3), HMS174, HMS174(DE3)pLysE, Origami(DE3), Origami, NovaBlue(DE3), NovaBlue, W3110(DE3), W3110, MG1655(DE3), MG1655, BW30384(DE3), BW30384.

Additionally, a host strain may contain a second vector that expresses T7 lysozyme. T7 lysozyme helps to increase the permeability of cells to substrates such as myo-inositol and products such as glucuronic acid. T7 lysozyme can be expressed from a plasmid such as pLysE or pLysS. MIO may be integrated into the chromosome of the bacterial cell. This may be done by using a transposon to insert the gene into the bacterial cell chromosome. This may also be done by the methods described in Datsenko and Wanner (Datsenko K A and Wanner B L, (2000) PNAS 97(12): 6640-6645. It may also be done using the methods based on sacB selection described in Reid, J L and Collmer, A, (1987) Gene; 57(2-3) 239-246.

Selection markers may be used to ensure that an incorporated MIO gene is maintained in the host bacterium. For example, a MIO DNA construct may be present on a high copy number plasmid. Such plasmids typically also contain a selectable marker. Suitable selection markers include antibiotic selection markers, auxotrophic selection markers, and markers that confer resistance or sensitivity to other chemicals, e.g., D-amino acid oxygenase, which confers resistance to D-ala and D-ser and sensitivity to D-ile and D-val.

Suitable antibiotic resistance markers include aminoglycoside phosphotransferase (APH[3']-II) which confers resistance to kanamycin and neomycin, and β-lactamase which confers resistance to ampicillin concentrations of 50-150 ug/ml and higher. Furthermore these markers can confer resistance to more than one antibiotic (for instance β-lactamase confers resistance to ampicillin and carbenicillin).

Suitable auxotropic selectable markers include metE (tetrahydropteroyltriglutamate homocysteine methyltransferase), trpA (the α subunit of tryptophan synthase), glnA (glutamine synthase), thrC (threonine synthase) and pyrE (orotate phosphoribosyl transferase).

In order to regulate and control production of MIO, an inducer may be used. Suitable inducers include lactose, arabinose, and isopropyl-beta-D-thiogalactopyranoside ("IPTG").

Other compounds may optionally be used in conjunction with the inducer selected in order to enhance the effect of the inducer. For example, ferric citrate may optionally be used in conjunction with an inducer.

In addition, the cells may be modified in other ways to optimize production of MIO. For example, cells may be modified to metabolize galactose so that both glucose and galactose, generated by lactose hydrolysis, can be used as nutrients. As another example, cells may carry modifications that inhibit or prevent metabolism of D-glucuronic acid, e.g., mutations in an uxaC locus. Such a modification can inhibit or prevent metabolism of D-glucuronic acid by cells in a lysate that survive the lysis procedure, thereby improving the yield of D-glucuronic acid in a conversion reaction.

III. Production of GGL from Myo-Inositol

The production of GGL from myo-inositol involves one or more of the following steps: fermentation of MIO-containing cells, lysis of MIO-containing cells to liberate MIO, activation of MIO from such cells, enzymatic conversion of myo-inositol to D-glucuronic acid using MIO, clarification, demineralization, heating, and recovery.

1) Fermentation

Fermentation of cells carrying a MIO gene may be carried out using batch methods, fed-batch methods, semi-continuous methods, or continuous methods of fermentation. Fermentation typically is optimized by controlling variables including temperature, pH, oxygen levels, and broth composition. Optionally, the cells may be transferred to another broth composition, or the broth composition may be changed over time.

Various measures of cell density may be used to determine the proper time for inducing the production of the myo-inositol oxygenase ("MIO") enzyme. Tests that can be done without removing material and minimally disturbing the broth, such as using optical density, are preferred.

After an appropriate time, depending on the method used, MIO will reach a level such that processing may continue. For example, the cells may be induced to start increased production of MIO. When MIO reaches the desired level, some or all of the cells may be harvested. Harvesting may be carried out by appropriate techniques such as filtration, centrifugation, etc. The cells may be washed during or following harvesting.

After harvesting, the cells may be stored for later use, or may be used directly. If desired, harvested cells may be separated from the liquid. Harvested cells, or the liquid containing cells, may be stored at between 0-10° C. for approximately 1 week or frozen for longer periods of storage, without significant degradation of MIO.

2) MIO Activation

One aspect of the present invention features a mixture used to prepare MIO prior to the introduction of myo-inositol. After the cells are harvested, the MIO enzyme in the cells may be prepared for use. MIO may be used in whole cells, or may be extracted by disrupting the cells. Cell disruption results in a suspension of broken cells with free, soluble MIO. If the cells are disrupted, it is not necessary to remove the cell debris before using the enzyme solution.

Whether the MIO is present in whole cells, or suspended in a mixture, the MIO will preferably be prepared before use. This preparation is often referred to as MIO activation. In order for the MIO enzyme to function most effectively and efficiently, the enzyme should first be activated. Activation increases the specific activity of MIO, making it more efficient at forming D-glucuronic acid. MIO specific activity may be measured in terms of the weight of D-glucuronic acid formed per weight of protein extract used.

A suitable activation mixture includes MIO and a reductant. Optionally, the activation mixture may also include Fe(II). Optionally, other components may also be present. In such a mixture, the MIO may be activated by using a chemical reducing agent or by providing an alternate source of reducing equivalents. Alternate reducing equivalents could be provided, for example, through the application of a voltage gradient to the mixture.

MIO may be present in the mixture at a concentration up to saturation, or may be present in excess of saturation. MIO may be present at a concentration greater than about 1 mg/ml, greater than about 2 mg/ml, greater than about 3 mg/ml, greater than about 5 mg/ml, greater than about 7 mg/ml, or greater than about 9 mg/ml. MIO may be present at a concentration less than saturation, less than about 200 mg/ml, less than about 150 mg/ml, less than about 100 mg/ml, less than about 75 mg/ml, less than about 50 mg/ml, or less than about 20 mg/ml.

MIO may be present in the mixture in whole cells, accompanied with cell lysate, in a purified cell lysate, or immobilized on a solid matrix. If MIO is present in whole cells, the cell wall and membrane should be permeable to allow the components of the mixture to pass through the cell walls and membrane and enable the MIO to be activated. Suitable whole cells include yeast cells, filamentous fungi cells, and Gram(+) and Gram(−) bacteria. If present in whole cells, MIO content may comprise from about 15% to about 50% by weight total soluble protein, from about 20% to about 50% by weight total soluble protein, or from about 25% to about 50% by weight total soluble protein.

Alternatively, the cells containing MIO may be lysed prior to addition of the MIO to the mixture. Lysed cells are cells that have been broken open by disruption of cell walls and cell membranes, which allows direct access of the MIO for activation. Cells may be lysed by mechanical or chemical action. Suitable means of mechanical disruption include sonication, freezing using liquid nitrogen, bead beating, French Press, or homogenizers such as a MICROFLUIDIZER® cell disruptor or a Gaulin-type homogenizer. Suitable compounds for chemical lysing include treatment with detergents such as BUGBUSTER® Extraction Reagent (an extraction reagent that gently liberates soluble proteins from *E. coli*, available from Novagen), treatment with lysozyme, or exposure to detergents such as TRITON® or TWEEN®. If the cells are lysed mechanically, the possible impact on the MIO may be minimized. Additionally, in some cases, higher enzyme concentrations are achieved using mechanical disruption.

Optionally, the cells may be chilled prior to the mechanical disruption of the cell. For example, the cells may be cooled to less than 20° C. prior to the mechanical disruption.

Optionally, the cells may be suspended in water or buffer prior to disruption. In some instances, the optional suspension in buffer may result in greater stability. It is also not required to remove all of the fermentation broth prior to optionally resuspending in water or buffer. Various suspension ratios and buffer concentrations may be used. Suitable suspension ratios include ratios of 3:1, 2:1, 1:1, 1:2, and 1:3 biomass in water or buffer. If buffer is to be used, examples of suitable buffer concentrations include 1 mM, 10 mM, 25 mM, 50 mM, 100 mM, and 200 mM. Suitable buffers include MOPS, HEPES, EPPS and sodium acetate. Furthermore, the removal of cell debris, for example by using centrifugation, is not necessary.

When cells are lysed, the contents of the cells are diluted into the lysis solution, but the percentages of protein remain unchanged. Therefore, in an unpurified cell lysate, MIO may comprise from about 15% to about 50% by weight total soluble protein, from about 20% to about 50% by weight total soluble protein, or from about 25% to about 50% by weight total soluble protein. The lysate may also be purified. Examples of suitable methods for purification include centrifugation and filtration. Purification, whether by centrifugation, filtration, or other means, removes some proteins from the lysate. Therefore, in a purified cell lysate, MIO may comprise from about 25% to about 100% by weight total soluble protein. MIO may also comprise at least 26%, 30%, 40%, 50%, 60% or more of the total proteins in a purified cell lysate.

A lysed cell mixture may be added either purified or unpurified into a mixture for MIO activation. If desired, samples containing MIO may be stored prior to use. Samples containing MIO may be stored at low temperatures for short periods of time or may be frozen for longer periods of storage without significant MIO degradation. For example, samples of purified $His_6$-tagged MIO, cell free extracts, and lysed biomass were put through 2 freeze-thaw cycles to −80° C. with no significant loss of activity. Additional freeze-thaw cycles, however, did reduce MIO activity. For long-term storage, MIO activity of samples remained stable after continuous storage at −80° C. for several months.

$His_6$-Tagged MIO can be purified in batches of ~200 mg of pure MIO. This purification may be done following the His Bind Kit User Protocol; Publication number TB054 Rev.D.0303 (available from Novagen). The lifetime of the pure enzyme may depend on various environmental factors, such as temperature, oxidative state, etc. In addition, lysed biomass was found to have approximately the same specific activity as cell free extracts.

Optionally, in some aspects, another component of the activation mixture may be iron. Typically, iron will be added to the activation as salts of Fe(II). Examples of suitable compounds containing Fe(II) include ferrous ammonium sulfate, ferrous sulfate, ferrous ascorbate, and ferrous halides such as ferrous chloride and ferrous iodide. Alternatively, a solution containing Fe(III) salts may be used. In such a case, Fe(III) should first be reduced to Fe(II), and then added to the solution containing myo-inositol oxygenase, in order to avoid potentially destroying the enzyme during the Fe(III) reduction reaction. Thus, Fe(II) may be present in the activation solution either by direct addition or following a reduction reaction.

Suitably, Fe(II) may be present at a concentration of 0 mM or greater. Fe(II) may be present in a concentration greater than about 0.2 mM, greater than about 0.5 mM, or greater than about 1 mM. Fe(II) may be present at a concentration less than about 50 mM, less than about 40 mM, less than about 30 mM, less than about 20 mM, less than about 15 mM, less than about 10 mM, less than about 7 mM, less than about 5 mM, or less than about 2 mM.

Another component of the activation mixture is a reductant. Typically, the reductant used in the activation of MIO has been cysteine. Cysteine has a reduction potential of −230 mV at pH 7. However, it has been found that substances other than cysteine may be used to efficiently and effectively activate MIO. Suitable substances include reductants having a reduction potential greater than about −200 mV. The substance may also have a reduction potential greater than about −150 mV, greater than about −100 mV, greater than about −50 mV, greater than 0 mV, or greater than 25 mV. The substance may also have a reduction potential less than about 500 mV, less than about 300 mV, less than about 200 mV, less than about 100 mV, or less than 75 mV. Other suitable substances include non-sulfur containing reductants. The non-sulfur containing reductant may be an organic, non-sulfur containing reductant. The reductant may be soluble in water. Examples of suitable reductants include ascorbic acid, isoascorbic acid, ascorbic acid 2-O-α-glucoside (Aα-2G), palmitoyl ascorbate, ascorbic acid 2-phosphate, 5 carbon analogs such as erythroascorbic acid, and derivatives thereof, including salts, esters, ethers, glycosides, phosphates, etc. More than one reductant may be used. The reductant used may include L-ascorbic acid or D-isoascorbic acid.

Various concentrations of reductant can be used. Reductant may be present at a concentration of 0 mM or greater, greater than about 0.5 mM, greater than about 1 mM, greater than about 2 mM, or greater than about 5 mM. Reductant may be present at a concentration less than about 1 M, less than about 900 mM, less than about 500 mM, less than about 100 mM, less than about 25 mM, or less than about 10 mM.

In addition to chemical activation, other types of MIO activation are also possible. For example, electrical activation of MIO may also be accomplished. In such a case, a voltage gradient will be applied to a mixture containing MIO and Fe(II) in order to activate the MIO. Optionally, chemical ions to enhance conductivity may be added to the mixture.

Other components may optionally be present in the activation mixture as well. Examples of other components which may be present include buffers, and other proteins and biomass.

Activation of MIO may be conducted in a buffer solution or in water. MIO activity level is about the same following incubations of cell free extracts over ice for 1 hour, whether the incubation is in water and unbuffered, or buffered. Examples of suitable buffers include 3-[N-morpholino]propanesulfonic acid ("MOPS") and sodium acetate. Optionally, if part of the mixture, buffer may be present at a concentration of up to 1 M. If part of the mixture, buffer may be present up to a concentration of 500 mM, up to 200 mM, or up to 100 mM.

As MIO may be obtained from lysed cells, other proteins and biomass may be present in the mixture. Typically, total soluble proteins present will be at a concentration from about 1 mg/ml to about 250 mg/ml.

During the activation process, the mixture should remain in a liquid state. Additionally, the incubation conditions should be suitably maintained for the activation reaction and MIO enzyme. Thus, temperatures may be maintained from about −5° C. to about 20° C., or from about 0° C. to about 10° C.

In addition, incubation time should be sufficient to activate the MIO enzyme. Suitable incubation times range from about 1 minute to about 10 hours, or longer. For example, incubation time may be from about 10 minutes to about 6 hours, or from about 15 minutes to about 150 minutes.

3) Enzymatic Conversion of myo-Inositol to D-Glucuronic Acid

The conversion of myo-inositol to D-glucuronic acid occurs in a mixture including MIO, myo-inositol, and oxygen. Optionally, other components may be present. Conversion of myo-inositol to D-glucuronic acid may be carried out as part of a batch process, a fed-batch or semi-batch process, a semi-continuous process, or a continuous process.

Preferably, MIO is activated prior to use in the reaction. The concentration of MIO may be up to saturation, and may even exceed saturation. Concentration will vary depending upon both the process and the addition method selected. For example, MIO may be added at the beginning of the conversion, it may be added periodically, or it may be added continuously to the reaction. Alternatively, the solution may be passed across MIO that is immobilized.

If added to the mixture, MIO may be present in whole cells, or may be freely available in the mixture. If MIO is present in whole cells, the whole cells may be present in a mixture, as a cell bed, or immobilized in some manner. Optionally, myo-inositol permeability may be enhanced by myo-inositol transporters (ITR1 and ITR2), chemical permeabilization, or expression of genes which increase permeability, such as the T7 lysozyme.

If not added as whole cells, MIO may be added to the mixture as a purified lysate or as an unpurified lysate. Unpurified lysate may contain other proteins and cell debris. Lysed biomass and cell free extracts have been found to have the same half-life during enzymatic oxidation of myo-inositol, and perform the oxidation at the same initial rate. Alternatively, MIO may be immobilized in some manner.

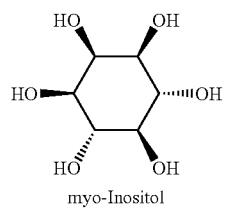

myo-Inositol

The substrate, myo-inositol, has the structure shown in the diagram above. Depending upon the process parameters chosen, myo-inositol may be added to the mixture in the beginning of the conversion process, periodically, or continuously throughout the conversion. Concentration will vary depending upon both the process and the addition method selected. However, myo-inositol may be present up to saturation, or even above saturation. Myo-inositol may be added as a liquid mixture, a slurry, or as a powder. Myo-inositol may be present at a concentration greater than about 1 g/l, greater than about 5 g/l, greater than about 10 g/l, greater than about 25 g/l, greater than about 50 g/l, or greater than about 100 g/l. Myo-inositol may be present at a concentration less than saturation, or less than about 500 g/l, less than about 450 g/l, less than about 400 g/l, less than about 300 g/l, or less than about 200 g/l. During the conversion, myo-inositol will be converted to D-glucuronic acid, and this will also affect the concentration of the myo-inositol in the mixture.

Examples of suitable myo-inositol material include NF12 grade (available from SinoChem Hebai Import and Export Corporation, Shijiazhuang, China) FCCIV grade (available from Changzhou Whole Fortune Pharmaceutical Co. Ltd, ChangZhou, China), and USP grade and crude myo-inositol from corn steep water (See U.S. Pat. No. 2,615,053).

Both USP grade (>99% pure myo-inositol), and crude myo-inositol (25 g/l myo-inositol-containing liquor (U.S. Pat. No. 2,615,053)) are suitable as substrates, as both substrates result in similar levels of oxidation in a reaction mixture. However, using crude myo-inositol may require additional purification treatments following the conversion, so as to minimize the impact on later process steps.

Oxygen is another component of the reaction mixture. Oxygen may be added to the reaction mixture as the process proceeds. The oxygen content in the mixture should be such that oxygen does not become a limiting factor in the conversion reaction. For example, oxygen may be present in sufficient quantity to support an oxygen utilization rate of 20 mmol per liter per hour or greater. Oxygen may be added to the mixture using many different methods. For example, the headspace above the reaction mixture may be continually renewed to maintain a high oxygen content. Alternatively, a gas including oxygen will be bubbled or sparged into the conversion mixture. Oxygen can be added as air, oxygen enriched air, or pure oxygen.

The dissolved oxygen ("DO") content of the mixture appears to affect the conversion rate, as mixtures having a higher DO have a faster conversion rate than those having lower DO levels. However, the final amount of product formed appears to be similar for mixtures having both high and low DO levels. Thus, it appears that varying the level of DO in the reaction medium affects the reaction rate, but has little effect on the total amount of product.

The temperature of the reaction mixture can also affect the rate of conversion. Suitably, the temperature will be from about 0° C. to about 50° C., from about 10° C. to about 35° C., from about 15° C. to about 30° C., or from about 15° C. to about 20° C. General temperatures between about 15° C. and 20° C. demonstrate the same rate of conversion. Temperatures deviating from this range, either cooler or warmer, have a decreasing rate and increasing loss of conversion as the temperature deviation increased. However, increasing the oxygen content to excess expands the temperature range from about 15° C. to about 30° C.

Prior literature reports indicated the need for Fe(II) in the reaction medium during the conversion of myo-inositol to D-glucuronic acid. However, a sample conversion having no additional Fe(II) added to the reaction medium showed no adverse effect on either the initial enzyme rate or the specific activity during the reaction.

Prior literature reports indicated the need for a reductant in the reaction medium during the conversion of myo-inositol to D-glucuronic acid. Mixtures containing no additional reductant added to the reaction medium showed little effect on either the initial enzyme rate or the total specific activity during the reaction. In fact, the initial rate of myo-inositol conversion showed a significant lag when additional reductant was added to the reaction medium compared to the rate of conversion in a reaction medium where no additional reductant was added.

Optionally, buffer or water may be added to the reaction mixture. Typically, an excess amount of buffer has been used to control the pH of the reaction mixture during conversion of myo-inositol to D-glucuronic acid. However, pH control using sodium hydroxide addition was also used to maintain the pH level. Using active pH control, water was found to be as effective as buffer during myo-inositol oxidation. Thus, the lack of buffer is not detrimental to the enzyme activity as long as the pH of the reaction medium is properly maintained.

Suitably, pH will be maintained greater than about pH 6.2, or greater than about pH 7.4. Suitably, pH will be maintained less than about pH 8.5, or less than about 7.6. Examples of suitable active pH control compounds include sodium hydroxide, potassium hydroxide, calcium hydroxide, and ammonium hydroxide.

Optionally, an antifoam agent may be added to the reaction mixture. This may be particularly desirable when oxygen is added to the reaction mixture using a sparging technique. Suitable antifoam agents include those that have minimal or no inhibitory effect on the MIO-catalyzed oxidation of myo-inositol. Examples of suitable antifoam agents include Sigma 204 (Organic antifoam), Sigma O-25 (Polyhydric alcohol; silicone polymer), Clerol FBA 265 (Alkoxylated polyol), Clerol FBA 975 (Alkoxylated glycerol transester), Ivanhoe XF8-1163B, or SAG 471. Examples of non-suitable antifoam agents include Sigma O-30(Fatty acid ester) and Clerol FBA 5057, as these did show a significant inhibitory effect.

Optionally, other additives may be added to the reaction mixture. For example, additives may be added to increase the reaction rate or activity of the MIO. Examples of rate additives include catalase, superoxide dismutase, bovine serum albumin, and calcium salts.

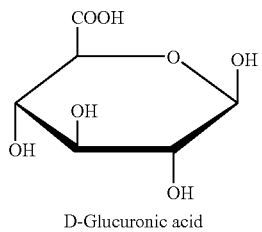

D-Glucuronic acid

The product, D-glucuronic acid, is shown above. The D-glucuronic concentration will vary depending upon the processing method used and the parameters selected for the enzymatic conversion. The concentration of D-glucuronic acid may be 0 g/l or greater, greater than about 0.1 g/l, greater than about 1 g/l, greater than about 2 g/l, greater than about 5 g/l, greater than about 10 g/l, or greater than about 20 g/l. The amount of the product, D-glucuronic acid, may reach or even exceed, saturation. D-glucuronic acid concentration may be greater than the myo-inositol concentration, and may be at least twice the myo-inositol concentration.

4) Clarification

At a desired time, the reaction mixture may be clarified to produce a clarified mixture. Suitable methods of clarifying the reaction mixture include vacuum filtration, centrifugation, ultrafiltration, membrane filtration, or other techniques that remove suspended solids. Product recovery may be increased by adding a washing step as part of the clarification process. Removing solids enables the later processes, such as demineralization, to proceed more efficiently, as the solids do not form deposits or interfere with the processes.

The suspended solid material may include insoluble proteins, and thus the clarification will typically also remove proteins from the mixture. The amount of proteins removed during clarification depends on various factors, including the method used for clarification, the temperature used, and the specific choices (such as pore size) utilized in the various methods. For example, applying a heat shock to the mixture before clarifying will often result in a greater reduction of protein content during clarification. In some instances, protein content of the reaction mixture may be reduced by 25%, 35%, or more by the clarification step.

5) Demineralizing

A reaction mixture or a clarified mixture can be demineralized to reduce or remove salts and ions from the mixture. Additionally, the protein content of the mixture may be further decreased during demineralization. Nearly any type of cation exchange resin may be used for demineralizing. An example of a suitable cation exchange resin is Relite C206.

Demineralization may be carried out at a reduced temperature, ambient temperature, or at elevated temperatures. When carried out at elevated temperatures, some of the resulting acid will be converted to a lactone.

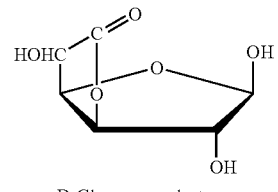

D-Glucurono-γ-lactone

6) Heating

A demineralized mixture can be heated to convert D-glucuronic acid to GGL, whose structure is shown above. Heating a mixture comprising D-glucuronic acid converts the organic acid to a lactone. Due to the presence of acid, the mixture has an acidic pH during heating. The extent of conversion depends upon various factors including the concentration of the acid, temperature of the mixture, and the time which the mixture is maintained at the temperature. Suitably, the temperature of the mixture will be above ambient temperature, or greater than about 50° C., 75° C., 90° C., or 120° C.

Heating may result in colorization of the mixture. In addition, color may be present as a result of earlier process steps, or from the feedstock material. Color may be removed from the heated mixture by treating with an appropriate material. For example, the mixture may be contacted with a decolorizing material such as powdered carbon, clay, diatomaceous earth, resins, or the like.

The heating step can be omitted if crystallization is performed through evaporative crystallization at some elevated temperature, e.g., 45° C. or higher, or 55° C. or higher. Under these conditions, lactonization and crystallization proceeds concomitantly.

7) Recovery

Product may be recovered from the reaction mixture, the clarified mixture, the demineralized mixture, or the heated mixture. Thus, either D-glucuronic acid or a salt of it or GGL may be recovered from the appropriate mixture. The product may be recovered by liquid separation techniques such as distillation, membrane diffusion, or crystallization.

GGL can be recovered from the mixture by crystallization. Crystallization of the GGL can be accomplished via concentrating and cooling the mixture. Concentration is preferably carried out under reduced pressure (less than atmospheric) to minimize color formation. One measure of concentration is the amount of dissolved solids present in the mixture. Suitably, the mixture will be concentrated to contain 25%, 33%, 50%, 60%, 67%, or more of dissolved solids. Additionally, crystallization is preferably carried out under reduced temperatures, in order to minimize color formation and maximize recovery. Suitably, the temperature will be less than about 100° C., less than about 75° C., less than about 50° C., or less than about 45° C. Following crystallization, GGL crystals can be removed from the mixture by appropriate methods including centrifugation, filtration, and the like.

In order to maximize recovery, the liquid remaining after crystallization can be subjected to additional processing. This additional processing includes subjecting the remaining mixture to repeated heating, concentrating, cooling, and recovery to convert remaining D-glucuronic acid to lactone and recover the lactone crystals. This can be repeated until the liquid is almost completely exhausted of acid or lactone.

IV. Uses and Advantages

Enzymatic conversion of myo-inositol to D-glucuronic acid has several advantages. The process avoids the use of large amounts of concentrated nitric acid. Thus, the environmental impact of the method is lessened, as there are no concentrated nitric acid waste streams and safety precautions required by the use of nitric acid are longer necessary. The process uses a lower value crop processing byproduct (myo-inositol) to generate a higher value product, D-glucuronic acid. The enzymatic conversion process generates significantly fewer waste by-products than current nitric acid processes. D-glucuronic acid generated by an enzymatic process appears to have fewer contaminating by-products, thus reducing the need for extensive downstream processing.

V. EXAMPLES

Example 1

MIO Assay Procedure

MIO activity was routinely determined using a modification of the method of Reddy et al (Reddy, C. C., Swan, J. S., Hamilton, G. A., *J. Biol. Chem.*, 256, 8510 (1981)). This assay is based on the reaction of orcinol with the product D-glucuronic acid. The standard assay mixture contained 50 mM MOPS, pH 6.5-6.6, 60 mM myo-inositol, and appropriate quantities of activated enzyme in a total volume of 0.5 mL. The enzyme was activated at total soluble protein concentrations of 20 mg/mL to 125 mg/mL by mixing with 5.0 mM ascorbate and 2.0 mM ferrous ammonium sulfate in 50 mM MOPS (approximately pH 6.5), and incubating on ice for 1-2 hours. The stock solutions of ascorbate (0.50 M dissolved in 0.5 M MOPS, pH 6.5) and the ferrous ammonium sulfate (0.50 M dissolved in $H_2O$) were prepared fresh daily. The activated enzyme was then added to a solution of myo-inositol and buffer stored on ice to initiate the enzymatic reaction. After vortex-mixing the components, the reaction was carried out in an air atmosphere at 15-30° C. with shaking at 250 rpm. Aliquots (5-300 µL) were removed at time intervals and added to a solution of trichloroacetic acid (345 µL final volume containing 45 µL of 20% trichloroacetic acid). After mixing by vortexing and centrifugation at 21,000 rpm for 3 min (at room temperature), 0.3 mL of the assay supernatant was transferred to a new 1.5 mL polypropylene microcentrifuge tube and analyzed for D-glucuronic acid formation.

A mixture including 0.3 mL of the assay supernatant, 0.6 mL of freshly prepared orcinol reagent (0.4% (w/v) orcinol, 0.09% (w/v) ferric trichloride hexahydrate in concentrated HCl) were added together, vortex-mixed, and then incubated in a boiling water bath for 30 min. After cooling to room temperature, the assay mixture was cleared by centrifugation at 21,000×g for 3 min. The supernatant was transferred to a disposable cuvette and the absorbance was measured at 660 nm. A standard curve was generated by replacing the product of the reaction with D-glucuronic acid (from 0 to 50 µg/mL) and carrying out the assay as described above. Standards were run of 0, 10, 26.67, 40 and 50 µg/ml D-glucuronic acid. All reactions were run in duplicate and the reactions were run with and without substrate when enzyme activity was low. The average of the absorbance readings of the assay mixtures carried out without substrate was subtracted from the average of readings of the assay mixtures containing substrate. The difference in the values was used to calculate the specific activity as µg D-glucuronic acid formed per mg protein per minute.

Total soluble protein concentration was estimated using the Bio-Rad Protein Assay Kit I (Bio-Rad catalog #500-0001) in a 96-well plate format. The total assay volume per well was 250 µL. Fifty µL of concentrated reagent was added to 200 µL of a sample or standard solution with immediate mixing. Bovine gamma globulin (Bio-Rad catalog #500-0005) was utilized for the standard curve determination (0 to 50 µg/mL). The absorbance of the assay samples and standards were measured at 595 nm. This assay is based on the Bradford dye-binding procedure with Coomassie brilliant blue G-250 (Bradford, M., *Anal. Biochem.*, 72, 248 (1976).

The concentration of D-glucuronic acid and myo-inositol were determined using a high performance liquid chromatography (HPLC) system with a refractive index detector. The system comprised of a Waters 2690 and a Waters 2414 refractive index detector. Separation of the two compounds was made using Aminex® HPX-87H, 300×7.8 mm ion exclusion column with isocratic elution at 35° C. The eluent was 0.01N sulfuric acid in water and the flow rate was 0.5 mL/min. Samples were analyzed after filtration through 0.2µ nylon filters. D-glucuronic acid and myo-inositol eluted at 9.65 and 11.25 minutes, respectively. The two analytes of interest were well resolved and no other compound was known to be co-eluted with either of the two. Multiple levels of standards confirmed good linearity over the concentration range of interest.

Example 2

Construction of Plasmids pCN-1 and pAN-1

*E. coli* DH10B ElectroMAX cells were purchased from Invitrogen Life Technologies, Inc. (Carlsbad, Calif.; Catalog #18290-015) and the plasmids pET23d and pET28a from Novagen Inc. (Madison, Wis.; catalog #69748-3). Restriction enzymes were purchased from New England Biolabs (Beverly, Mass.). Bacterial growth media components were from Difco or Fisher Scientific, and other reagents were of analytical grade or the highest grade commercially available. DNA electrophoresis was carried out using a Bio-Rad Mini-Sub Cell GT system (Hercules, Calif.; Catalog #170-4405). An Eppendorf Mastercycler Gradient (Hamburg, Del.) thermal cycler was used for PCR experiments. UV-visible spectrometry was performed using a Ultrospec 3100 pro (Biochrom Ltd., Cambridge, England). Electroporations were performed using a Bio-Rad Gene Pulser II system. Primers were purchased from Integrated DNA Technologies, Inc (Coralville, Iowa). Automated DNA sequencing was carried out by Agencourt (Beverly, Mass.).

Six µg of pET30a containing the *Cryptococcus neoformans* mio gene (See Example 6 or WO 02/074926 A2 for details) were digested with NcoI/XhoI overnight while 2.5 µg of pET23d were similarly digested overnight with NcoI/XhoI followed by an additional 2 hour digestion with Calf Intestinal Alkaline Phosphatase ("CIP"). The digested DNA samples were gel purified from a 1% agarose gel using a QIAquick Gel Extraction kit (Qiagen Inc.; Valencia Calif.; Catalog #28704) and each sample was eluted in 30 μl of EB buffer (10 mM Tris Cl (pH 8.5)). One hundred and twenty ng of XhoI/NcoI digested mio (*Cr. neoformans*) was ligated to 120 ng of XhoI/NcoI/CIP digested pET23d using the Rapid DNA Ligation Kit (Roche Molecular Biochemicals; Indianapolis, Ind.) to generate the vector construct pET23d:mio (*Cr. neo*). The resulting ligation mix to generate the pET23d:mio (*Cr. neo*) construct was desalted using a QIAquick PCR Purification kit (Qiagen Inc.; Valencia Calif.; Catalog #28104) and eluted in 30 μl of EB buffer. Transformation of 1 μl of the ligation mix into electrocompetent DH10B was performed under standard conditions described in the Bio-Rad electroporation manual for gram negative bacteria. Clones containing the putative pET23d:mio (*Cr. neo*) construct were identified by NcoI/XhoI restriction analysis and confirmed by sequencing.

Similarly, a pET28a:mio (*Cr. neo*) construct was generated using NcoI/XhoI digested *Cryptococcus neoformans* gene and NcoI/XhoI/CIP digested pET28a vector. The ligation and transformation conditions into electrocompetent DH10B cells were the same as those described above. Clones containing the putative pET28a:mio (*Cr. neo*) construct were identified by NcoI/XhoI restriction analysis and confirmed by sequencing. One μl of the pET28a:mio (*Cr. neo*) construct was transformed into chemically competent *E. coli* B834 (DE3), BLR(DE3), BL21(DE3), (Novagen Inc.; Madison, Wis.; Catalog #69041-3, #69053-3 and #69450-3, respectively), BL21-AI and BL21Star(DE3) (Invitrogen Life Technologies; Carlsbad, Calif.; Catalog # C6070-03 and # C6010-03, respectively) according to the manufacturers directions. Putative transformants were screened by NcoI/XhoI restriction analysis.

In order to provide an auxotrophic selection marker system, the metE gene was inserted into the vector pET23d:mio (*Cr. neo*).

PCR primers specific for the *E. coli* metE gene were designed and the desired gDNA fragment was amplified from *E. coli* DH10B genomic DNA sample that was prepared using the Puregene DNA purification system (Gentra Systems; Minneapolis, Minn.).

```
Primers:
5' primer:    5'-CGCGGCCGGCTTACTTCGATCATGAAAGTC-3'

3' primer:    5'-CGCGGCCGGCAGAAGTCGCTGTAATGAGAA-3'
(NgoMIV restriction sites are underlined)
```

PCR Conditions included the following. The reactions contained 1 μM final concentration of each primer, 0.2 mM of dATP, dCTP, dGTP, and dTTP, 2.5 units of Expand High Fidelity PCR Polymerase (Roche Molecular Biochemicals), 5 μl of 10× Expand buffer (with MgCl$_2$) and 200 ng of *E. coli* gDNA (strain DH10B) in a 50 μl reaction. The thermocycler program utilized a hot start of 96° C. for 2 minutes; followed by 30 cycles of a denaturing step at 96° C. (30 sec), an annealing step at 52.5° C. (1 min), and an extension step at 68° C. (3 min 30 sec) and finally a finishing step at 72° C. (7 min); Six independent 50 μl PCR reactions were pooled and the amplified DNA with an approximate size of 2.5 Kbp was purified using a QIAquick PCR clean-up kit and eluted in 30 ml of EB buffer, yielding ~17 μg of PCR product. Four μg of the metE PCR product were digested with NgoMIV overnight. A 2.5 μg sample of previously generated pET23d:mio (*Cr. neo*) was similarly digested overnight with NgoMIV followed by a 2 hour incubation with CIP. The digested DNA samples were gel purified from a 1% agarose gel using a QIAquick Gel Extraction Kit and eluted in 30 μl of EB buffer. A 56 ng sample of digested, purified pET23d:mio(*Cr. neo*) was ligated to 160 ng of the digested, purified metE PCR product using the Rapid DNA Ligation Kit (Roche Molecular Biochemicals) to generate the vector construct(s) pCN. The resulting ligation mix to generate the pCN construct was desalted using a QIAquick PCR Cleanup Kit and eluted in 30 μl of EB buffer. Transformation of 1 μl of the ligation mix into electrocompetent DH10B was performed as described above. Clones containing the putative pCN construct(s) were identified by EcoRV restriction analysis. Since cloning of the metE gene was non-directional two alternative constructs resulted. The pCN-7 construct (EcoRV digestion yielded DNA fragments of ~1.0 Kbp and ~6.0 Kbp) denoted a construct in which the metE gene and the *Cryptococcus neoformans* mio gene were both transcribed in the same directions while the pCN-1 construct (EcoRV digestion yielded DNA fragments of 2.5 Kbp and ~4.5 Kbp) denoted a construct in which the metE gene and the *Cryptococcus neoformans* mio gene were transcribed in opposite orientations. Both constructs were confirmed by DNA sequencing.

One μl of the pCN-1 construct was transformed into chemically competent *E. coli* B834(DE3) and HMS174(DE3) (Novagen Inc.; Madison, Wis.; Catalog #69041-3 and #69453-3, respectively) according to the manufacturers directions. Putative transformants were screened by NcoI/XhoI restriction analysis.

An analogous plasmid (pAN-1) was constructed which expressed the mio gene from *Aspergillus nidulans*. The *Aspergillus nidulans* mio open reading frame was amplified by PCR using conditions similar to those described above and the following primers:

```
5'-CCATACATGTCGCCTCACTCCAACG-3'

5'-GGCCCTCGAGCTACCACTTGATCTGCTTATTAGGGAAGAAC-3'
(PciI and NcoI sites are underlined)
```

The template used was the *A. nidulans* fosmid clone 8223 B10 from the Fungal Genetics Stock Center, University of Kansas Medical Center. The resulting PCR product was gel purified from a 1% agarose gel using a QIAquick Gel Extraction kit and digested with PciI/XhoI. The digested PCR product was then desalted using a QIAquick PCR Cleanup Kit.

The pCN-1 construct was digested with NcoI/XhoI/CIP as described above to remove the *Cryptococcus neoformans* mio and gel purified from a 1% agarose gel using a QIAquick Gel Extraction Kit. The *A. nidulans* mio was ligated to the NcoI/XhoI/CIP digested pCN-1 construct using a Rapid DNA Ligation Kit (Roche Molecular Biochemicals) to generate the vector construct(s) pAN-1. The resulting ligation mix to generate the pAN-1 construct was desalted using a QIAquick PCR Purification kit and eluted in 30 μl of EB buffer. Transformation of 1 μl of the ligation mix into electrocompetent DH10B was performed under standard conditions described in the Bio-Rad electroporation manual for gram negative bacteria. Clones containing the putative pAN-1 construct were identified by SmaI restriction analysis and confirmed by sequencing.

One μl of the pAN-1 construct was transformed into chemically competent *E. coli* B834(DE3) (Novagen Inc.; Madison, Wis.; Catalog #69041-3) according to the manufacturers directions. Putative transformants were screened by NcoI/XhoI restriction analysis.

Figure 8:
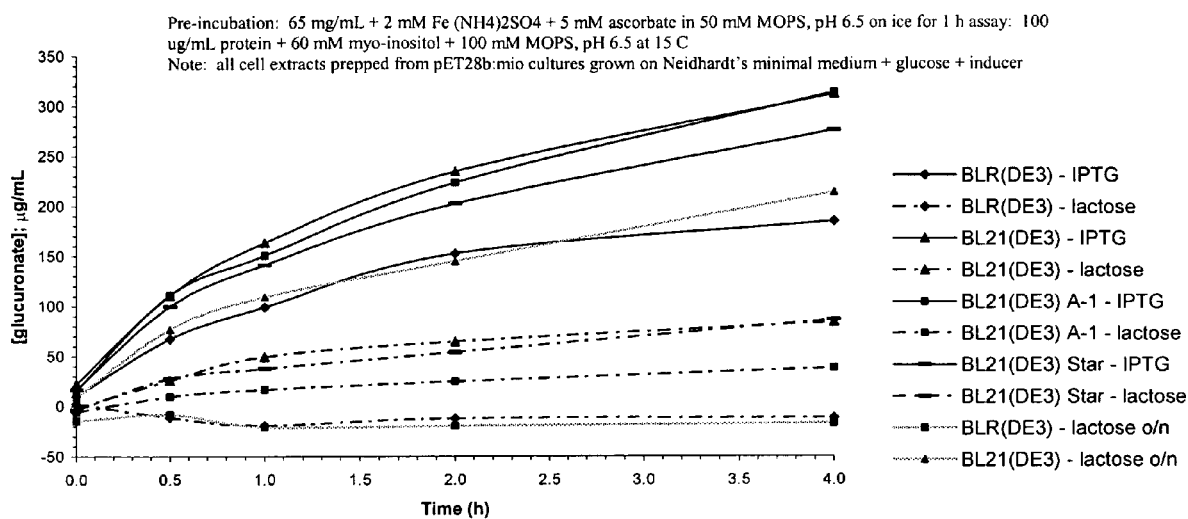
FIG. 8 is a graph showing the myo-inositol oxygenase activity over time using PET28b:mio in various host strains.

FIG. 8 shows activity levels for MIO from various host strains.

Example 3

Production of Myo-Inositol Oxygenase (MIO) in Batch Fermentations

Myo-inositol oxygenase was produced in fermentors at the 4-L scale, in a batch process that achieves higher cell densities than those obtained in flasks. A culture of the strain *E. coli* BLR(DE3)::pET28b carrying the gene for expression of the *Cryptococcus neoformans* oxygenase (pET28a:mio (*Cr. neo*)), was cultured to demonstrate this effect. Starting from a frozen culture stock, the cells were: (1) grown in 25 ml of Luria-Bertani broth ("LB") with 50 μg/ml kanamycin, at 37° C. and 250 rpm for 6-8 hours; (2) transferred to 200 ml of the same medium at the same conditions; and (3) the cell mixture was used to inoculate a fermentor containing 4 liters of medium composed of (per liter): 2 g $(4)_2SO_4$; 1.6 g $KH_2PO_4$; 9.9 g $Na_2HPO_4$-$7H_2O$; 0.65 Na citrate; 20 g NZ amine A; 20 g glucose; 0.24 g $MgSO_4$ and 50 mg kanamycin. The fermentation was maintained at 37° C., air was supplied at 2 liters per minute and the agitation was adjusted to maintain the dissolved oxygen above 40% saturation. The pH was controlled at 7.0 with an ammonium hydroxide solution. When the optical density ($OD_{600}$) reached 3 units, the temperature was reduced to 30° C., 30 μM ferric citrate was added, and the production of the enzyme was induced by the addition of 0.4 mM IPTG. The cell paste was harvested by centrifugation 4 hours after induction. Under these conditions, 5.9 g/L dry cell weight (DCW) were obtained. The expression of MIO was followed by SDS gel electrophoresis and estimated at 20-25% of the total protein at the end of the fermentation, slightly lower than the results observed in growth in flasks at low cell density. Enzyme activity was measured as described in Example 1.

Example 4

Production of Myo-Inositol Oxygenase (MIO) in Fed-Batch Fermentations

In order to increase the amount of MIO produced in the fermentation process, a fed-batch protocol was developed. It was used with several different *E. coli* strains. The protocol and results for growth of *E. coli* strain B834(DE3)::pCN-1 are described below. The inoculum was grown starting from a frozen culture stock into 25 ml of LB broth with 100 μg/ml ampicillin, at 37° C. and 250 rpm for 6-8 hours; It was then transferred to 200 mL of Neidhardt minimal medium and incubated under the same conditions for 12-16 hours. This medium contains (per liter): 8.37 g MOPS; 0.72 g Tricine (N-Tris(hydroxymetyl)-methyl glycine), 5 ml 1.9 M $NH_4OH$; 1 ml 0.276 M $K_2SO_4$; 0.025 ml 0.02 M $CaCl_2$.$2H_2O$; 0.21 ml 2.5M $MgCl_2$.$6H_2O$; 10 ml 5 M NaCl; 10 ml 0.132 M $K_2HPO_4$ and 0.02 ml Neidhardt micronutrients solution. The Neidhardt micronutrients solution contained: 0.18 g/L $(NH_4)_6(MO_7)_{24}$.$4H_2O$; 1.24 g/L $H_3BO_3$; 0.36 g/L $CoCl_2$.$6H_2O$; 0.12 g/L $CuSO_4$.$5H_2O$; 0.80 g/L $MnCl_2$.$4H_2O$; and 0.14 g/L $ZnSO_4$.$7H_2O$ When the $OD_{600}$ reached about 2 units, the culture was transferred to a fermentor at a 5% ratio. The fermentation medium consisted of: 2.0 g/L$(NH_4)_2SO_4$; 8.0 g/L $K_2HPO_4$; 2.0 g/L NaCl; 1.0 g/L $Na_3Citrate$.$2H_2O$; 1.0 g/L $MgSO_4$.$7H_2O$; 0.025 g/L $CaCl_2$.$2H_2O$; 0.05 g/L $FeSO_4$.$7H_2O$; 0.4 ml/L Neidhardt micronutrients and 2.0 g/L glucose. Two to three hours after inoculation, an exponential glucose feed was set up using a 60% glucose solution. The feed was supplied at the required rate to support microbial growth at an exponential rate of 0.15 $h^{-1}$. When the $OD_{600}$ reached a value of 30 (around 20 hours after inoculation, corresponding to a cell biomass of 15-16 g DCW/L), the temperature was reduced to 30° C., 30 μM ferric citrate was added and the feed was switched from glucose to a mixture of 50% glucose and 10% lactose. This exponential feed was maintained for 8 hours. At the end of the fermentation the cell concentration was 28 g DCW/L, with an enzyme expression level of about 25% of the total protein.

Example 5

Effect of Different Variables on Cell Growth and Enzyme Expression

Using the fed-batch protocol described in Example 4, several different variables were tested to improve cell density and enzyme expression. Some of the variables and their effect are described below:

Effect of induction scheme. A comparison was done between: (1) a slow induction with a continuous feed of a mixture of glucose and lactose (control); (2) a one time addition of 20 g/l lactose followed by a continuous exponential glucose feed; and (3) a one time addition of 1 mM IPTG, followed by the same glucose feed. The results are shown in Table 1, and indicate that induction with lactose is very efficient for this particular strain and construct, and avoids the requirement of expensive IPTG.

TABLE 1

| Condition | Final DCW (g/L) | Enzyme activity per unit of fermentor volume (% of control) |
|---|---|---|
| Case 1 | 28.1 | 100 |
| Case 2 | 24.4 | 85 |
| Case 3 | 31.7 | 90 |

Effect of lactose concentration and feed rate after induction. In order to examine different induction schemes, variations in lactose addition were tested. The lactose was added as a single dose of 20 g/L, using a 10% lactose/50% glucose mix, or using a 20% lactose/40% glucose mix. Additionally, there was a reduction in the feed rate after induction to support a growth rate not higher than 0.1 $h^{-1}$ to avoid the accumulation of glucose in the broth. The results are shown in Table 2. Reducing the feed rate after induction allowed for higher protein production, and the slow addition of lactose also seemed to contribute to increased expression of the enzyme.

TABLE 2

| Condition | Final DCW (g/L) | Enzyme activity per unit of fermentor volume (% of control) |
|---|---|---|
| Control (after induction: μ = 0.15 $h^{-1}$, feed 10% lactose/50% glucose) | 28.1 | 100 |
| Reduced feed rate (after induction: μ = 0.1 $h^{-1}$, feed 10% lactose/ 50% glucose) | 23.7 | 144 |
| Reduced feed rate (after induction: μ = 0.1 $h^{-1}$, single lactose addition 20 g/L) | 21.3 | 93 |

TABLE 2-continued

| Condition | Final DCW (g/L) | Enzyme activity per unit of fermentor volume (% of control) |
|---|---|---|
| Reduced feed rate, higher lactose (after induction: $\mu = 0.1\ h^{-1}$, feed 20% lactose/40% glucose) | 22.4 | 137 |

Effect of temperature. The effect of the temperature during the two phases of the fermentation (before and after induction) was studied in three different temperature schemes: (1) the cells were grown at 37° C., and the temperature was reduced to 30° C. at the time of induction; (2) the cells were grown at 37° C. throughout the fermentation; and (3) the cells were grown at 30° C. throughout the fermentation. The results are shown in Table 3, and demonstrate that growth at 30° C. was equally effective for enzyme accumulation as growth at 37° C. followed by lower temperature during induction. Maintaining 37° C. after induction was detrimental for enzyme activity.

TABLE 3

| Condition | Final DCW (g/L) | Enzyme activity per unit of fermentor volume (% of control) |
|---|---|---|
| Scheme (1) | 26.9 | 100 |
| Scheme (2) | 27.1 | 64 |
| Scheme (3) | 28.6 | 100 |

Test of different enzymes and host strains. Using the protocol described in Example 4, modified with the reduction in feed rate to support a growth rate of $0.1\ h^{-1}$ after induction, the production of enzymes from two different sources as well as different host cells was evaluated for enzyme expression. Some of those results are summarized in Table 4.

TABLE 4

| Condition | Final DCW (g/L) | Enzyme activity per unit of fermentor volume (% of control) |
|---|---|---|
| E. coli B834 (DE3)::pCN-1 (Cyptococcus neoformans enzyme) | 23.7 | 100 |
| E. coli B834(DE3)::pAN-1 (Aspergillus nidulans enzyme) | 23.6 | 34.5 |
| E. coli HMS174(DE3)::pCN-1 (Cyptococcus neoformans enzyme) | 21.4 | 109.4 |

Example 6

Biocatalytic Production of D-Glucuronic Acid from Myo-Inositol

A small-scale protocol was used to develop the biocatalytic production of glucuronic acid from myo-inositol. Cells containing myo-inositol oxygenase were grown as described before, harvested by centrifugation and washed in 50 mM MOPS buffer at pH 7.0. The cell paste was kept frozen until use. To prepare the enzyme for the reaction, the cells were resuspended in 2 volumes of the same buffer at pH 6.5 and broken using either a French press or a MICROFLUIDICS® homogenizer (MICROFLUIDIZER® cell disruptor M-110L, available from Microfluidics, MA). Breakage was accomplished by 2 to 3 passes at 20,000 psi, and was followed visually using a microscope. The cell extract was centrifuged for 20 minutes at 15,000 rpm to remove the cell debris. Total soluble protein was measured in the clear supernatant, as described in Example 1. The cell extract was diluted to a protein concentration of 75 mg/ml and the enzyme was incubated for 1 hr on ice in the presence of ascorbic acid and ferrous ammonium sulfate at concentrations of 5 and 2 mM, respectively.

The enzyme reaction was carried out in 0.7 L reactors with temperature, pH, agitation and dissolved oxygen control. A solution of 50 g/L myo-inositol in 50 mM MOPS at pH 6.5 (200 mL) was used in the standard protocol. Temperature was controlled at 15° C. Pure air, air enriched with oxygen or pure oxygen were used to supply enough oxygen for the reaction to proceed. The air was supplied either in the headspace of the reactor or was sparged into the liquid. The formation of glucuronic acid results in a decrease in the pH of the broth. To keep the pH at the desired value, pH 6.5, the acid was neutralized with 4 N NaOH. The enzyme solution was added to reach an initial concentration of 2 g soluble protein/L. The reaction proceeded very fast immediately after the enzyme addition and the rate decayed over time. Different experiments varied the number and/or amount of enzyme additions. The progress of the reaction was followed by HPLC analysis.

Figure 2:
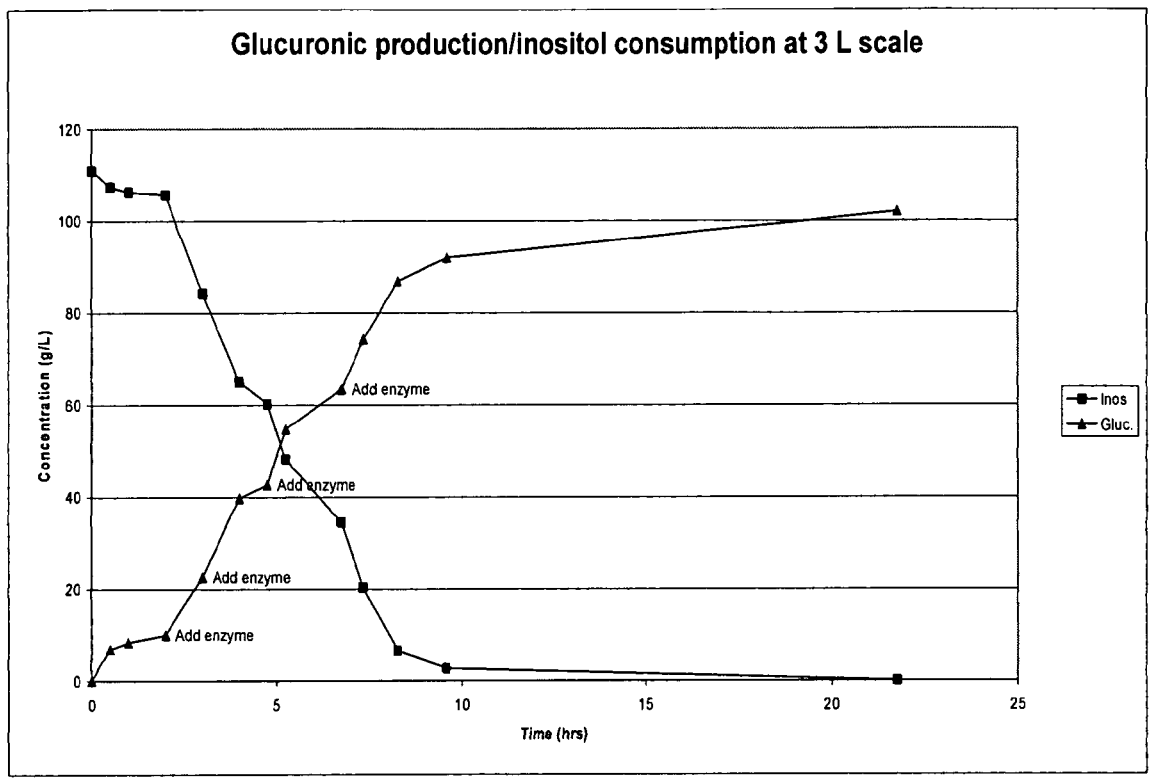
FIG. 2 is a graph showing the concentrations over time of the reactant and product during a reaction conducted according to one aspect of the described process.

FIG. 2 is a graph showing the concentrations over time of the reactant and product in a reaction process.

The impact of several parameters on the reaction performance was studied using this protocol.

Effect of dissolved oxygen. Different dissolved oxygen ("DO") levels were maintained in the reaction by blowing either oxygen enriched air or pure oxygen in the overhead space, or by bubbling air through the broth in the presence of an antifoam. The agitation was maintained at a constant rate.

In a set of experiments where the DO was maintained at either less than 5% or more than 20% saturation, it was determined that excess oxygen was a preferred condition. While 30 g/L of glucuronic acid were produced in 8 hours and 33 g/L in 25 hours in the presence of excess oxygen, only 10 g/L and 22 g/L were produced when oxygen was limiting.

In a subsequent experiment the effect of a highly oxidative environment was tested by maintaining pure oxygen in the reactor headspace instead of air. It was determined that pure oxygen was not detrimental to the enzyme, and that the reaction proceeded much faster using pure oxygen. While only 7 g/L glucuronic acid were produced in 2 hours in the presence of air, 13 g/L were produced with oxygen. However, the final conversion percentage remained the same when measured at 22 hours. Similar results to those produced by the use of pure oxygen were obtained by sparging air through the broth, which allowed the dissolved oxygen to remain above 50% throughout the reaction.

Figure 3:
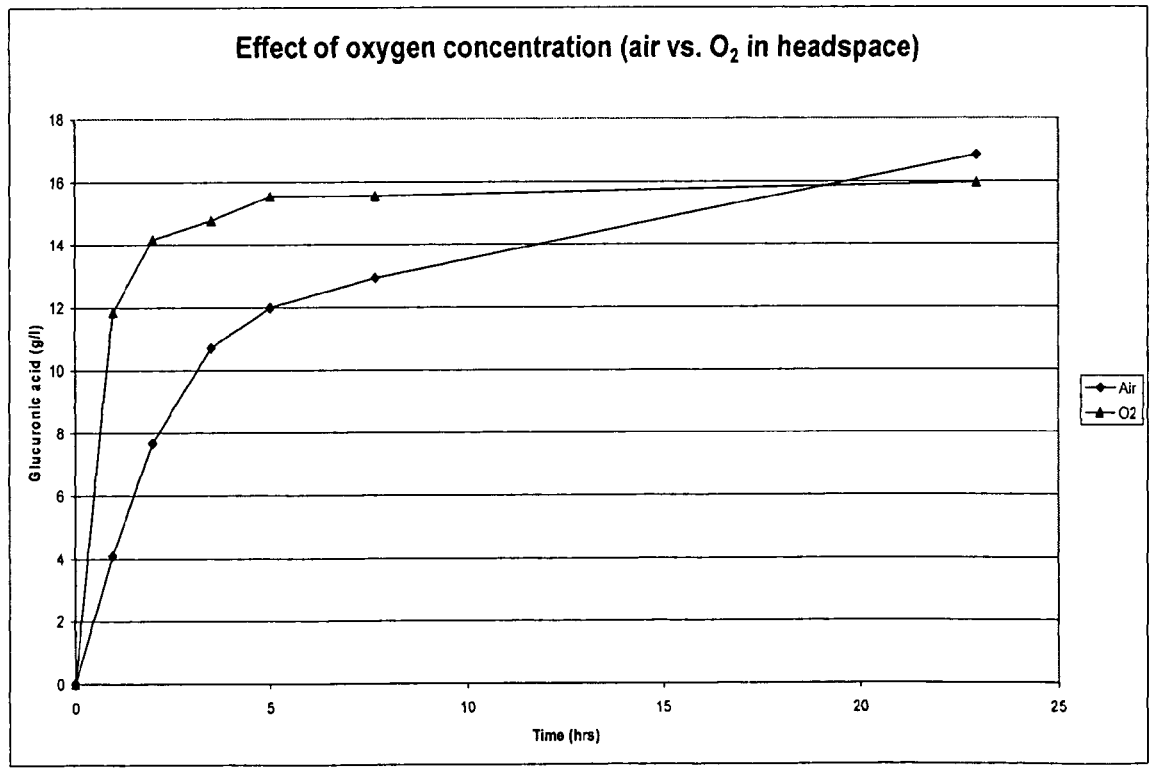
FIG. 3 is a graph showing the relative effect of pure oxygen and air on the reaction process.

FIG. 3 shows the relative effect of oxygen and air used in the reaction process.

Effect of pH. The effect of the pH of the cell extract during the enzyme incubation with iron and a reductant, and that of the pH during the reaction were studied in separate experiments.

During enzyme incubation, the pH of the cell extract was adjusted to different values from pH 6.0 to pH 8.0 before the addition of ascorbic acid and iron, and was maintained at that value during the incubation. No difference in enzyme activity was observed for cell extracts incubated between 6.0 and 7.0, while a small decrease was measured in cell extracts incubated at pHs above pH 7.0.

A series of tests were conducted to determine the effect of pH during the reaction. The cell extract was incubated at pH 6.5, and the pH during the reaction was controlled at pH 6.0, pH 6.5, pH 7.0, pH 7.5, pH 8.0, and pH 8.5. A significant difference in activity was found depending on the pH of the reaction. The results are shown in Table 5. Further optimization testing indicated that the optimum pH for the reaction was in the range from about pH 7.4 to pH 7.6.

TABLE 5

| pH of the reaction | Glucuronic acid production as % of control |
| --- | --- |
| 6.0 | 72 |
| 6.5 | 100 |
| 7.0 | 170 |
| 7.5 | 206 |
| 8.0 | 190 |
| 8.5 | 96 |

Effect of the enzyme concentration and cell debris. The effect of the initial enzyme concentration was studied at 1.87, 2.80 and 3.75 g protein/L, and also compared with the addition of non-centrifuged cell extract. The final concentration of D-glucuronic acid after 5 hours was proportional to the amount of enzyme added, with values of 25.1, 39.8 and 51.9 g/L, respectively. The amount of D-glucuronic acid produced in the presence of cell debris was identical to that produced with clarified cell extract.

Figure 5:
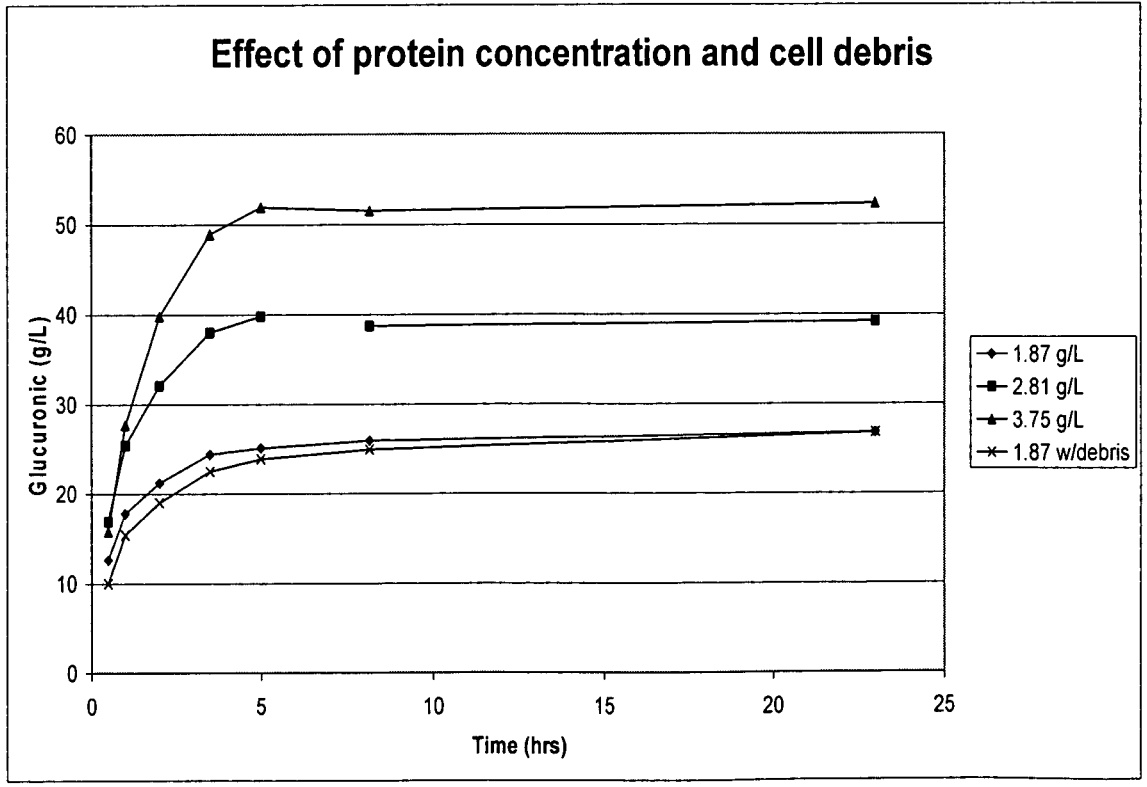
FIG. 5 is a graph showing the relative effect of enzyme concentration and cell debris on the reaction process.

FIG. 5 is a graph showing the relative effect of concentration and cell debris.

Effect of buffer concentration and ionic strength. The effect of the buffer concentration was tested with the described protocol of Example 6, and included testing without any buffer, using 5 mM MOPS, and using 50 mM MOPS. No difference in the performance of the reaction was observed, either in reaction rate or in extent of reaction, as long as good pH control was provided.

Additionally, further studies on increasing the ionic strength of the broth by adding salts, using either NaCl or sodium glucuronate at 0.25 M and 0.5 M, or mixes of both, indicated better enzyme performance at higher ionic strength. About a 50% increase in initial reaction rate and final concentration of D-glucuronic acid produced was observed at salts concentrations higher than 0.25 M. Some inhibition was detected with high concentrations of commercial sodium glucuronate, but when D-glucuronic acid produced by this method was mixed with NaCl to achieve a salt concentration of 0.5 M, an 80% increase in D-glucuronic acid produced was obtained.

Effect of temperature. Although the initial studies indicated that the enzyme activity was preserved longer at 15° C. than at higher temperatures, this effect was further studied at the 200 ml scale with the protocol described above in Example 6. It was determined that there was no difference in enzyme activity between 15° C. and 20° C., but at 25° C., about 50% less glucuronic was produced over a 24 hour period. However, it was verified that when the reaction was performed with enough oxygen supply to ensure maximum reaction rate, and the enzyme required to complete the reaction was added in aliquots, the same amount of enzyme was required to reach complete conversion of up to 100 g/L myo-inositol for temperatures ranging from 15° C. to 30° C.

Effect of Substrate Concentration.

Figure 4:
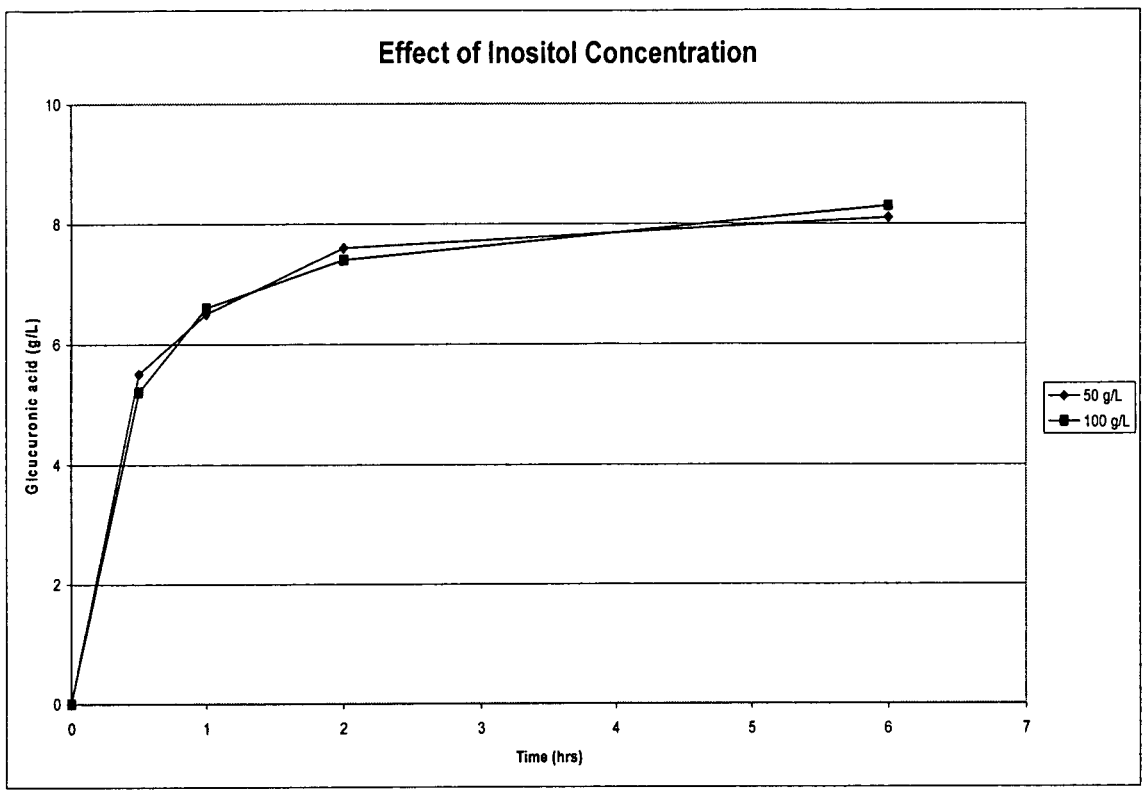
FIG. 4 is a graph showing the effect of myo-inositol concentration on the reaction process.

FIG. 4 shows the effect of myo-inositol concentration on the reaction process. No difference in enzyme activity was found with myo-inositol concentrations between 50 and 100 g/L. Further testing indicated that myo-inositol concentrations up to saturation (160 g/L) can be used without negative impact on the enzyme.

Example 7

Production of D-Glucuronic Acid at 3 Liter Scale

This example describes the complete protocol for the production of D-glucuronic acid from myo-inositol by biocatalysis with myo-inositol oxygenase.

E. coli B834(DE3), carrying the pCN-1 expression plasmid was grown in a 3-liter fermentor in a fed-batch mode as described in Example 4, with the improved conditions described in Example 5. The temperature was maintained at 30° C., the growth rate was controlled at 0.15 $h^{-1}$ before induction, but the mixed feed of 50% glucose and 10% lactose used during induction was supplied at a rate that would support a maximum growth rate of 0.1 $h^{-1}$. The biomass was harvested by centrifugation 8 hours after induction. The cell paste obtained, with about 22% dry solids, was frozen at −80° C. until further use.

A 150 g sample of cell paste was resuspended in a total of 450 ml of 5 mM MOPS at pH 7.0 and run 3 times through a MICROFLUIDIZER® cell disruptor (at 20000-21000 psi), while maintaining the temperature below 20° C. Total soluble protein in the cell extract was measured at 80 mg/ml. This cell extract can be frozen at 80° C. and will maintain activity for at least several months.

The cell extract was thawed the day of the experiment. The enzyme was incubated in a mixture of 5 mM MOPS at pH 6.5, containing 2 mM ferrous ammonium sulfate and 5 mM ascorbate for between 1 hour and 2.5 hours, at a concentration of 35 mg/ml protein.

A solution of 150 g/L myo-inositol in water was placed in a 4 liter reactor, with temperature, pH and dissolved oxygen control. The temperature was maintained at 20° C., the pH was controlled at 6.5 with 4 N NaOH, air was sparged at 0.5 liters per liter of reactor per minute, and the agitation was adjusted sufficiently high to maintain excess dissolved oxygen at all times during the reaction. SAG 471 antifoam (0.5 mL/L) was added for foam control. After incubation, the enzyme solution was added in steps over a period of 7 hours, and the reaction was allowed to continue for 29 hours. The enzyme was initially added at a concentration of 3.7 g soluble protein per liter of initial reactor volume, and three more additions of 1.7 g/L soluble protein per liter of initial reactor volume each were done over the course of 7 hours. The reaction was followed by base and oxygen consumption and HPLC measurements of D-glucuronic acid produced and myo-inositol consumed.

According to the base utilization, 90% of the reaction was completed in 16.8 hours, 95% in 21.8 hours, and 99% at 25.5 hours. At 29 hours, the myo-inositol had been completely consumed and glucuronic acid was the only component detected by HPLC. Given the dilution of the broth caused by the addition of enzyme and base, the final glucuronic acid concentration was measured at 107 g/L. This material was used for further purification of the D-glucuronic acid and production of glucurono-γ-lactone.

Example 8

Clarification

The above described reaction mixture was clarified over a ceramic membrane with a pore size of 0.2 microns, which resulted in a clear liquor. The product recovery was maximized through washing of the concentrate, as described below. In the clarification process the protein content of the reaction mixture decreased 40%.

A typical filtration was carried out as follows:

| Microfiltration on Ceram inside ATZ membrane 0.2μ (220 cm²). | |
| --- | --- |
| Supply: | 3500 g @ 10.45% ds |
| Soluble N content: | 4616 ppm based on DS (dry solids) (0.45μ filtered sample) |
| Glucuronic acid: | 97.8 g/l |

After filtration and washing of the concentrate with 500 ml water, 3805 g filtrate@9.65% DS and 196.7 g of concentrate at 7.1% DS were obtained.

The absorbance of the filtrate in a 1 cm cuvette at 660 nm was 0.009 and the nitrogen (N) content (ppm based on DS) was 2912. Nitrogen determination was done with the Total Nitrogen analyzer TN-100 from Mitsubishi Chemical Corporation Example 9

Demineralization

A typical demineralization was carried out as follows:
Demineralization of the filtrate of Example 8 was done over 1.8 L strong cation resin (Relite C260), at a flow rate of 3.4 L/h, with 1850 ml of water-used for washing the resin. An amount of 4404.6 g of demineralized product was obtained at 6.5 Brix with a N content (ppm on DS) equal to 2040 and pH=1.7

Example 10

Heating

The major impurity in the refined liquor is the MOPS that is used during the enzyme preparation. A typical composition after refining is shown on Table 6.

After heating at 120° C. for 30 minutes, part of the acid was converted to a lactone and the composition shown in on Table 6 was obtained. Heating at lower temperatures, such as at 95° C. over the same time period, led to similar compositions.

TABLE 6

| | Unknown 1 | Glucuronic Acid | Intemediate | Glucurono-γ-lactone | Unknown 2 | MOPS |
| --- | --- | --- | --- | --- | --- | --- |
| After Demineralization | 0.02% | 98.37% | 0.21% | 0.59% | 0.00% | 0.80% |
| After Heating | 0.72% | 47.63% | 3.83% | 46.72% | 0.14% | 0.96% |

Color was removed from the liquor by treating with powdered carbon at 60° C. for 40 minutes at a dose of 1 g carbon/100 g DS, followed by filtration over a Buchner funnel precoated with 40 g of Celite diatomite product. The color, as measured by absorbance at 420 nm, was reduced from 1.94 to 0.22

Example 11

Crystallization

The liquor from Example 10 was concentrated to 68% dissolved solids by reducing the pressure while maintaining a temperature of 55° C. After concentrating the mixture, the mixture was cooled from 55° C. to 40° C. This resulted in formation of GGL crystals, which were then recovered through centrifugation of the mixture. In this way, 86.5% of the lactone that was in solution was recovered as pure crystalline glucurono-γ-lactone. This represents 40% of the total acid and lactone present in the solution.

Through heating, concentration, cooling, and centrifugation of the mixture, additional crystals were recovered. The use of this method of repetition enabled 55.2% of the D-glucuronic acid to be recovered as pure GGL crystals. Additionally, 22.9% of the D-glucuronic acid was also recovered as impure glucurono-γ-lactone crystals, that can be purified further by additional recrystallization. Thus, the total recovery of D-glucuronic acid as GGL crystals was 78.1%.

Example 12

Reduction Potential Calculation

The reduction potential for ascorbic acid is determined using the method of Ball (Ball E G, (1937) Studies on Oxidation-Reduction XXIII. Ascorbic Acid, J. Biol. Chem., 118: 219-2391937) in which ascorbic acid (0.002 M) in sodium acetate buffer (0.1 M) is titrated with ferricyanide (0.04 M) in the presence of the mediator thionine (0.001 M). Briefly, the components are mixed and flow into a chamber containing a series of electrodes. After flowing past the last electrode the mixture forms a junction with a solution saturated with potassium chloride that is in direct contact with a saturated potassium chloride calomel half-cell. The observed potentials from the electrodes are extrapolated to zero time. The recorded potentials are standardized to the hydrogen standard. Using this method the reduction potential of ascorbic acid is +54 mV at 25° C. and +51.2 mV at 30° C., as calculated and shown by Williams and Yandell (Williams N H & Yandell J K, (1982) Outer-Sphere Electron-Transfer Reactions of Ascorbate Anions, Aust. J. Chem., 135:1133-1144.1982).

Figure 7:
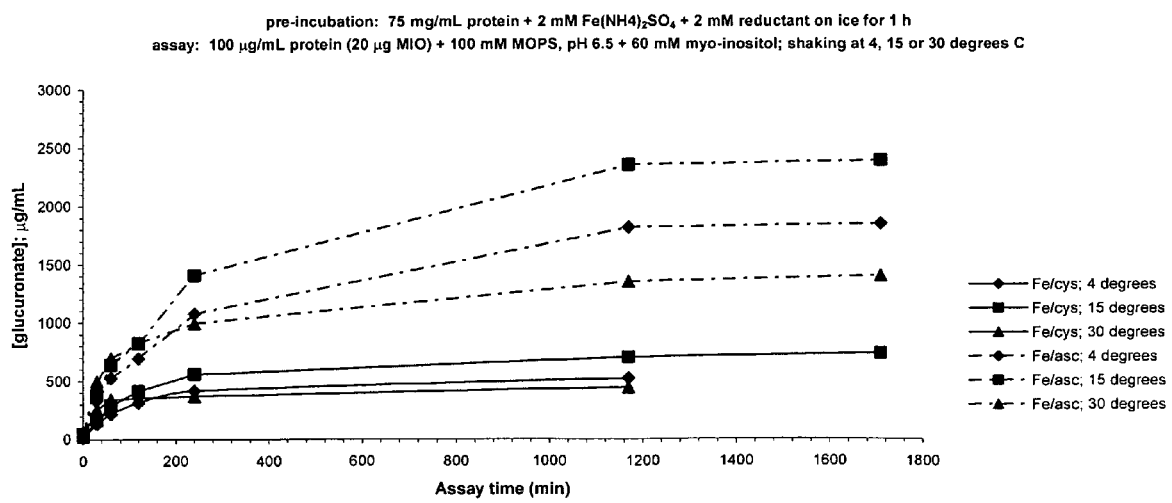
FIG. 7 is a graph showing the effectiveness of cysteine and ascorbate on the activation of myo-inositol oxygenase.

FIG. 7 compares the effectiveness of cysteine and ascorbate on MIO activation.

Example 13

Antifoam Effect on MIO Activity

Figure 6:
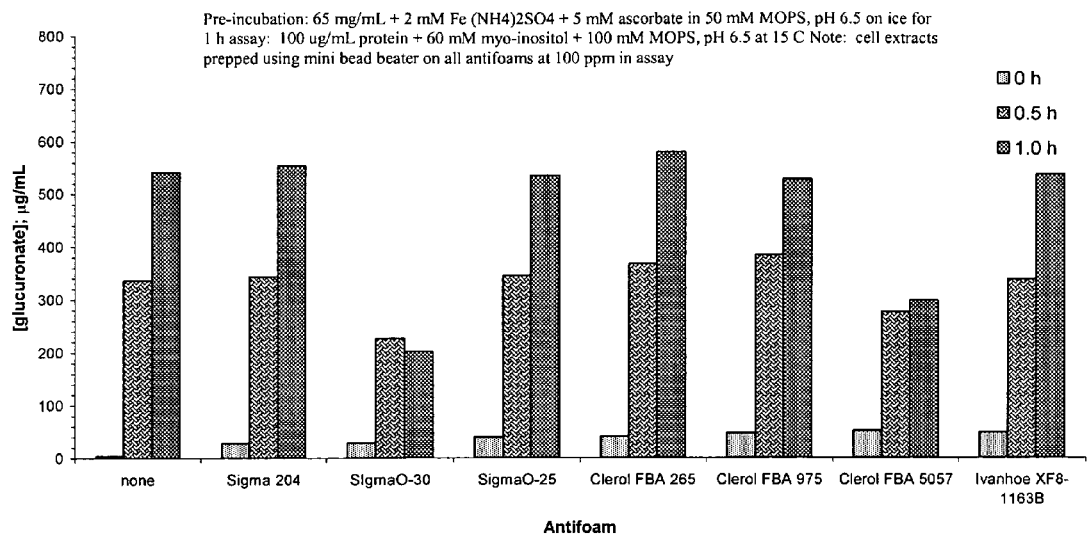
FIG. 6 is a graph showing the relative effect of antifoams on the reaction process.

FIG. 6 is a comparison chart demonstrating MIO activity when various antifoams are used in a reaction mixture assayed as described in Example 1.

Example 14

Conversion Rate Additives

Bovine serum albumin and Ca(II) salts were found to have minimal effect on MIO specific activity and conversion rate. However, catalase was found to increase MIO activity, as a conversion mixture including catalase showed an 18% improvement in conversion after 6.5 hours. Superoxide dismutase was also tested and found to slightly increase MIO activity after 6.5 hours. The combination of both catalase and superoxide dismutase were tested together in a conversion mixture, and showed a 26% improvement in conversion after 6.5 hours. Although the conversion rate increased, the final conversion percentages were similar to conversion mixtures without those same additives.

Example 15

Protein Concentration

Samples of cell free extract were activated in a mixture using various protein concentrations. The protein concentrations used were 25 mg/ml, 75 mg/ml, and 125 mg/ml. The mixture using a protein concentration of 75 mg/ml resulted in the highest level of MIO activity.

Example 16

Incubation Time Period

Samples of cell free extract were activated in a mixture with 2 mM Fe(II) and 5 mM L-ascorbate. The mixture was incubated on ice during the activation reaction. The incubation time was varied, and times of 20, 70, 130, 190 and 250 minutes were used, with the activity being measured after each incubation period. The highest activity was measured after an incubation of 20 minutes, while the lowest activity was measured after 130 minutes. The highest activity using a 20 minute incubation period showed approximately 25% better activity than lowest activity measured. However, no general trend was apparent between 20 and 120 minutes.

Example 17

Substrate Concentration

MIO activity was tested using increasing concentrations of USP grade myo-inositol substrate. MIO showed at least 50% more activity when the substrate consisted of ~8.5% dry solids myo-inositol compared to ~1% dry solids myo-inositol.

Example 18

Activity Loss

SDS-PAGE analysis of reaction mixtures, showed well-defined bands of the appropriate molecular weight for MIO, at 5 and 7 hours after commencing the reaction process. These results indicate that the observed loss of enzyme activity in a reaction over time was not due to the action of proteases.

Example 19

Product Inhibition

In order to test the effect of concentration of product in the conversion, cell free extract was used to convert 5 mM myo-inositol to D-glucuronic acid in the presence of up to 180 g/l (0.93 M) of commercially available D-glucuronic acid (Sigma Chemical, catalog #G-5269, St. Louis Mo.). MIO activity under these conditions was ~50% of the activity of MIO assayed in the absence of added D-glucuronic acid.

In a conversion mixture having 60 g/l of added D-glucuronic acid (0.31 M), in which the D-glucuronic acid was prepared according to Example 6, MIO had 92.5% of the activity seen in the absence of added D-glucuronic acid. In this reaction, MIO converted 100% of the myo-inositol to product.

These results may indicate that a composition comprising D-glucuronic acid made by the process described in Example 6 differs from other commercially available glucuronic acid compositions, as MIO activity was affected differently by the two compositions.

Example 20

Plasmid Construction

E. coli DH10B ElectroMAX cells were purchased from Invitrogen Life Technologies, Inc. (Carlsbad, Calif.; Catalog #18290-015). Restriction enzymes were purchased from New England Biolabs (NEB; Beverly, Mass.). Bacterial growth media components were from Difco or Fisher Scientific, and other reagents were of analytical grade or the highest grade commercially available. DNA electrophoresis was carried out using a Bio-Rad Mini-Sub Cell GT system (Hercules, Calif.; Catalog #170-4405). Protein electrophoresis was carried out using a Bio-Rad Mini PROTEAN 3 Electrophoresis Cell (Catalog #165-3301). An Eppendorf Mastercycler Gradient (Hamburg, Del.) thermal cycler was used for PCR experiments. UV-visible spectrometry was performed using a Ultrospec 3100 pro (Biochrom Ltd., Cambridge, England). Electroporations were performed using a Bio-Rad Gene Pulser II system. Primers were purchased from Integrated DNA Technologies, Inc (Coralville, Iowa). Automated DNA sequencing was carried out by Agencourt (Beverly, Mass.).

Part I: Tandem Rare Arginine Codon Repair

The pCN-1 vector was used as a template to generate a modified form of the *Cryptococcus neoformans* mio gene in which two rare arginine codons were mutated to common *E. coli* arginine codons. Mutagenic PCR primers to replace the tandem rare arginine codons at positions 139 and 140 (CGA CGA) with common *E. coli* arginine codons (CGC CGT) were synthesized following the guidelines described in the QuikChange II XL Site-Directed Mutagenesis Kit (Stratagene catalog #200522; La Jolla, Calif.). The sequence of the two primers was:

```
Primer 1:
5'-CGCTGAGGCTATTCGCCGTGACGGCAAGCCTGAATG-3';

Primer 2:
5'-CATTCAGGCTTGCCGTCACGGCGAATAGCCTCAGCG-3'.
```

Tandem arginine codons are underlined.

The *Cryptococcus neoformans* mio gene carried on the pCN-1 vector was mutagenized using the above described PCR primers in the following PCR reaction mix:

| | |
|---|---|
| 10× Reaction Buffer: | 5 µL |
| pCN-1 vector template (18 ng/µL): | 0.5 µL |
| Primer 1 (10 µM): | 1.0 µL |
| Primer 2 (10 µM | 1.0 µL |
| dNTP's (10 mM each): | 1.0 µL |
| Quik Solution: | 3.0 µL |
| Water: | 38.5 µL |
| Pfu Polymerase (2.5 U/µL): | 1.0 µL |

The thermocycler was operated under the following conditions:

| 1) | 95° C. | 1 minute |
|---|---|---|
| 2) | 95° C. | 50 seconds |
| 3) | 60° C. | 50 seconds |
| 4) | 68° C. | 8 minutes |
| 5) | Repeat steps 2-4 17 times | |
| 6) | 68° C. | 7 minutes |
| 7) | 4° C. | Hold |

Following PCR, the reaction mixture was digested with 1 μL of DpnI restriction enzyme (10 U/μL) for two hours. The reaction mix was desalted using a QIAquick® PCR Purification Kit (QIAGEN #28104; Valencia, Calif.) following the manufacturers directions and the DNA product was eluted in 30 μL of EB Buffer. Three μL of the eluent was electroporated into 20 μL DH10B ElectroMAX cells and allowed to recover for one hour before plating on LB+ampicillin (100 μg/mL). Plasmid DNA was purified from liquid cultures (LB+ampicillin) of individual colonies using a QIAprep® Spin Miniprep Kit (QIAGEN #27106) and screened by restriction digestion with BsmBI. Wild-type pCN-1 yields two fragments of ~5.9 Kbp and ~1.2 Kbp, while the codon optimized product yields a single linearized ~7.1 Kbp DNA fragment. In addition, the mutagenesis of the mio gene was confirmed by automated DNA sequencing. This vector was named pCN (RR)-1.

Part II: PsiI Restriction site Insertion at Beta-Lactamase (bla) 3' Terminus

The pCN-1 vector was used as a template to insert a PsiI restriction site at the 3' terminus of the beta-lactamase gene (bla). Insertion of this site provides a convenient means of deleting bla when used in combination with the already-existing PsiI site upstream of the beta-lactamase transcriptional promoter. Mutagenic PCR primers to insert the PsiI site were synthesized following the guidelines described in the QuikChange II XL Site-Directed Mutagenesis Kit (Stratagene, La Jolla, Calif.). The sequence of the primers was:

```
Primer 1:
5'-GATAGGTGCCTCACTGATTAAGCATTTATAACTGTCAGACC-3'

Primer 2:
5'-GGTCTGACAGTTATAAATGCTTAATCAGTGAGGCACCTATC-3'.
```

The PsiI site is underlined.

The PsiI site was inserted into the pCN-1 vector using the above described PCR primers under the PCR conditions similar to those described above. Following PCR, the reaction mixture was digested with DpnI, eluted as described above. Three μL of the eluent was electroporated into 20 μL DH10B ElectroMAX cells as described above. Plasmid DNA was purified from liquid cultures (LB+ampicillin) of individual colonies and screened by restriction digestion with PsiI. Wild-type pCN-1 yielded a single linearized ~7.1 Kbp DNA fragment while the mutagenized product yielded two fragments of ~6.0 Kbp and ~1.1 Kbp. In addition, the second PsiI site of the mutagenized product was confirmed by DNA sequencing. This vector was named pCN(Psi)-1.

Part III: Construction of a Plasmid Containing the pCN (RR)-1 Mio Gene and Lacking the Bla Gene Plasmids pCN(RR)-1 and pCN(Psi)-1 (3 μg each) were each digested with NcoI and XhoI according to the manufacturer's directions. After 1 h of incubation at 37° C., 2 U of shrimp alkaline phosphatase (Roche Molecular Biochemicals; Indianapolis, Ind.) was added to the pCN(Psi)-1 reaction and the incubation was continued for 1 h. The mio gene band (~1 Kbp) from pCN(RR)-1 and the vector band (~6 Kbp) from pCN(Psi)-1 were purified from a 1% agarose gel. The purified DNA products were quantified by measuring the absorbance at 260 nm and ligated using a Rapid DNA Ligation Kit (Roche Molecular Biochemicals) at a molar ratio of vector to gene insert of 1 to 5. The ligation mixture was desalted and eluted from the spin column with 30 μL of 0.5×EB buffer. Transformation of the ligation reaction (1 μL) into DH10B ElectroMAX cells (20 μL) was performed under standard conditions using a 0.1 cm cuvette and a Bio-Rad Gene Pulser II system as described in the Bio-Rad electroporation manual. After recovery for one hour at 37° C., the transformation mix was plated on LB+ampicillin (100 μg/mL). The plates were incubated overnight at 37° C. Plasmid DNA was purified from liquid cultures (LB+ampicillin) of individual colonies using a QIAprep® Spin Miniprep Kit and screened by restriction digestion for the mutagenized mio gene insert (BsmBI digestion) and the second PsiI site in the vector. This new vector was named pCN (RR-psi)-1.

The vector pCN(RR-psi)-1 was digested with PsiI according to the manufacturer's directions. The vector band (~6 Kbp) was purified from a 1% agarose gel and self-ligated using a Rapid DNA Ligation Kit. The ligation mixture was desalted, eluted from the spin column with 30 μL of 0.5×EB buffer, and stored at −20° C. until transformed into a methionine auxotroph host. This new vector was named pCNAR.

Example 21

Construction of E. coli K-12 Hosts

The E. coli strain BW25113ΔmetE, which has an insertion of a chloramphenicol resistance marker (cat) gene into the metE locus, was constructed using the gene inactivation method of Datsenko and Wanner (Proc. Natl. Acad. Sci. USA 97: 6640-5, 2000). E. coli strains BW25113/pKD46 and BW 25141/pKD3 were obtained from the E. Coli Genetic Stock Center, New Haven, Conn., and electrocompetent cells of BW25113/pKD46 were produced as described by Datsenko and Wanner in the presence of 1 mM arabinose to induce the recombination functions on pKD46. The cat gene of pKD3 was amplified using the following primers:

```
5'-AAAAATGACAATATTGAATCACACCCTCGGTTTCCCTCGCGTGTAGG
CTGGAGCTGCTTC-3';
and

5'-GTGGTATTACCACCCGGTTTGGATTTTACCCCCGACGCAACATATGA
ATATCCTCCTTAG-3'.
```

Underlined nucleotides correspond to the regions in the E. coli chromosome immediately upstream and downstream of the metE locus, respectively. Non-underlined nucleotides are homologous to regions in pKD3 that permit amplification of a fragment containing the cat gene. The primers were used in a PCR reaction with pKD3 as template.

The PCR product was digested with DpnI, purified, concentrated, and transformed into BW25113/pKD46 expressing the recombination functions. Transformants were plated on LB plates containing 25 μg/mL chloramphenicol.

Chloramphenicol-resistant transformations were single-colony purified on non-selective LB medium, and single colonies tested for retention of chloramphenicol resistance, loss of ampicillin resistance (indicating curing of pKD46), and requirement for methionine for growth on M9-glucose minimal medium. Confirmation of correct insertion of the cat gene into the metE locus was carried out by colony PCR of the resultant metE::cat strain using primers that flank the insertion locus (GGTGCGTTGGCTGCGTTTCT; and GCTGGCAGCGTATGCTGGAATG).

A BW25113ΔompT strain was similarly constructed. The cat gene of pKD3 was amplified using primers:

<u>GATTACCTGGCGGAAATTAAACTAAGAGAGAGCTCTATGAATCCT</u>GTGTAGGCTGGAGCTGCTTC;
and

<u>CTATTTTGCAGTCACAACCTGCATACCAGACGGTTCATTTTGCAG</u>CATATGAATATCCTCCTTAG, where the underlined nucleotides correspond to the regions in the *E. coli* chromosome immediately upstream and downstream of the ompT locus, respectively, and the non-underlined nucleotides are homologous to regions in pKD3 that permit amplification of a fragment containing the cat gene. A PCR reaction was carried out using plasmid pKD3 as template. The PCR product was precipitated with ethanol, digested with DpnI, purified with the QIAquick PCR Purification Kit and transformed into BW25113/pKD46 expressing the recombination functions. Transformants were plated on LB plates containing 25 μg/mL chloramphenicol.

Chloramphenicol-resistant transformations were single-colony purified on non-selective LB medium, and single colonies tested for retention of chloramphenicol resistance, and loss of ampicillin resistance (indicating curing of pKD46). Confirmation of correct insertion of the cat gene into the ompT locus was carried out by colony PCR of the resultant ompT::cat strain using primers that flank the insertion locus (TTGCGAGGCCTTATGTGTCT; and TATGGTGTCACGCCATCTCA).

DE3 lysogenation: Integration of the λDE3 prophage into the BW30384 strain was done using a Novagen λDE3 Lysogenation Kit (Novagen, Madison, Wis.). Both the lysogenation and verification of lysogeny were conducted according to manufacturer's protocols.

Lysate production: P1 phage lysates were made for the BW25113ΔmetE and BW25113ΔompT strains, to allow transfer of the knockouts into the BW30384(DE3) production host. Donor strains were grown overnight in LB medium containing 10 μg/mL chloramphenicol. The culture was used to inoculate 5 mL of fresh medium containing 5 mM CaCl$_2$, using a 1:10 dilution. The subculture was grown 70 minutes at 37° C. One mL of culture was incubated with 100 μL of a phage stock at room temperature for 20 minutes. The phage/culture was then mixed with 4 mL of soft agar containing 5 mM CaCl$_2$ and overlaid on LB medium. Good plaque formation was observed after approximately 5 hours. The soft agar was scraped into a centrifuge tube and pooled with 1 mL of LB used to rinse the plate. Five drops of chloroform were added to the tube, which was shaken and placed at room temperature for 20 minutes. The mixture was then centrifuged at 10,000 g for 10 minutes and the supernatant filtered with a 0.2 um syringe filter. All lysates were stored at 4° C.

Transduction into a production host: The metE knockout was transferred to the BW30384(DE3) strain by P1 phage transduction. BW25113(DE3) was grown overnight in LB medium containing 10 μg/mL chloramphenicol. The culture was used to inoculate 5 mL of fresh medium containing 5 mM CaCl$_2$, using a 1:20 dilution. The subculture was grown 70 minutes at 37° C. The culture was centrifuged, resuspended in 500 μL MC buffer (0.1M MgSO$_4$, 5 mM CaCl$_2$), and incubated at room temperature for 20 minutes. Various dilutions of the donor lysate (1/100 to 1× in MC buffer) were added in equal volume to 100 uL of culture. The mixtures were incubated for 20 minutes at 37° C., after which 200 uL of citrate buffer and one mL of LB were added to each. Citrate buffer contained 0.1M citric acid and 220 mM NaOH adjusted to pH 5.5. The cultures were grown at 37° C. for one hour with shaking, followed by centrifugation. Cell pellets were resuspended in 100 uL of citrate buffer and plated on LB medium containing 10 μg/mL chloramphenicol.

Chloramphenicol-resistant colonies were single-colony purified on selective medium and single colonies were tested by PCR, as previously described for the BW25113 knockout strains, to verify the transfer of the metE knockout. Primers homologous to the bacteriophage T7 RNA polymerase locus were also used to confirm the presence of the prophage. Primer sequences GTGGCATAAGGAAGACTCTATTC and CCTTTGGTCATATCGTTACCTTG produce an amplification product 717 nucleotides in length from prophage template. The metE chloramphenicol insertion was then looped out according to the procedure described by Datsenko and Wanner (2000). The ompT knockout described above was then transferred to the BW30384(DE3)ΔmetE strain using procedures as described above to generate the production host strain BW30384DE3ΔmetE ΔompT(cat).

The ompT chloramphenicol insertion cassette was removed according to the procedure described by Datsenko and Wanner (2000) using pCP20, a temperature-sensitive replication and bla-containing plasmid that shows thermal induction of FLP recombinase enzyme synthesis. The resulting strain BW30384(DE3)ΔompTΔmetE was tested for loss of resistance to chloramphenicol and ampicillin (curing of pCP20), and for the requirement of methionine (added at 0.1 mg/mL) during growth on Neidhardt minimal medium (described in Example 4) with glucose (4 mg/mL).

A BW25113ΔuxaC strain was constructed using a similar method to that used for BW25113ΔompT and BW25113ΔmetE. *E. coli* strain BW 25141/pKD4 was obtained from the *E. Coli* Genetic Stock Center, New Haven, Conn. The kan gene of pKD4, which confers resistance to kanamycin, was amplified using primers 5'-

5'-<u>GCCCGCCGTCTGTATCACGACTACGCAAAAGACCAGCCGA</u>CATATGAATATCCTCCTTAG-3'
and

5'-<u>CCGATCATCTGGCACAGAATGCGGCGGAAGTATTCGTGAC</u>GTGTAGGCTGGAGCTGCTTC-3', where the underlined nucleotides correspond to the regions in the *E. coli* chromosome at the 5' and 3' ends of the uxaC locus, respectively, and the non-underlined nucleotides are homologous to regions in pKD4 that permit amplification of a fragment containing the kan gene. Three PCR reactions were carried out using Expand High Fidelity PCR System (Roche Molecular Biochemicals Catalog #1 732 650) with added PfuTurbo® DNA polymerase (Stratagene), and pKD4 vector as template. The three PCR reactions were run at annealing temperatures of 50, 53 and 56° C.

The PCR products were purified from a 1% agarose gel. All PCR reactions generated similar amounts of product and were combined after extraction from the gel. The combined PCR products were then digested with DpnI, purified, and transformed into BW25113/pKD46 expressing the recombination functions. Transformants were plated on LB plates containing 25 μg/mL kanamycin.

Kanamycin-resistant transformations were single-colony purified on non-selective LB medium and single colonies were tested for retention of kanamycin resistance and loss of ampicillin resistance (indicating curing of pKD46). Confirmation of correct insertion of the kan gene into the uxaC locus was carried out by colony PCR of the resultant uxaC::kan strain using primers that flank the insertion locus (5'-GTGCTAATTCGGCTTCCGTA-3'; and 5'-ATGTCCACGAGCAACATCCT-3').

Lysate production: P1 phage lysates were made for the BW25113ΔuxaC strain, to allow transfer of the uxaC knockout into the BW30384(DE3)ΔompTΔmetE(cat) production host. The BW25113ΔuxaC(kan) strain was grown overnight in LB medium containing 25 μg/mL kanamycin. The culture was used to inoculate 5 mL of fresh medium containing 5 mM $CaCl_2$, using a 1:10 dilution. The subculture was grown 70 minutes at 37° C. One mL of culture was incubated with 100 μL of a phage stock at room temperature for 20 minutes. The phage/culture was then mixed with 4 mL of soft agar containing 5 mM $CaCl_2$ and overlaid on solid LB medium. Good plaque formation was observed after approximately 4 hours. The soft agar was scraped into a centrifuge tube and pooled with 1 mL of LB used to rinse the plate. Several drops of chloroform were added to the tube, which was shaken and placed at room temperature for 20 minutes. The mixture was then centrifuged at 10,000 g for 10 minutes and the supernatant was filtered with a 0.2 um syringe filter. The lysate was stored at 4° C.

Transduction into a production host: The uxaC knockout was transferred to the BW30384(DE3)ΔompTΔmetE(cat) strain by P1 phage transduction. The recipient strain was grown overnight in LB medium containing 10 μg/mL chloramphenicol. The culture was used to inoculate 5 mL of fresh media containing 5 mM $CaCl_2$, using a 1:20 dilution. The subculture was grown 70 minutes at 37° C. The culture was centrifuged, resuspended in 500 μL MC buffer (0.1 M $MgSO_4$, 5 mM $CaCl_2$), and incubated at room temperature for 20 minutes. Various dilutions of the donor lysate (0.01 to 1× in MC buffer) were added in equal volume to 100 μL of culture. The mixture was incubated for 20 minutes at 37° C., after which 200 μL of citrate buffer and 1 mL of LB were added. Citrate buffer contained 0.1M citric acid and 220 mM NaOH adjusted to pH 5.5. The cultures were grown at 37° C. for one hour with shaking, followed by centrifugation. Cell pellets were resuspended in 100 μL of citrate buffer and plated on solid LB medium containing 25 μg/mL kanamycin.

Kanamycin-resistant colonies were single-colony purified on selective medium and single colonies were tested by PCR, as previously described for the BW25113 knockout strain, to verify the transfer of the uxaC knockout to generate the strain BW30384(DE3)ΔompTΔmetEΔuxaC(cat,kan).

The ompT chloramphenicol and the uxaC kanamycin insertion cassettes were then removed according to the procedure described by Datsenko and Wanner (2000) using pCP20. The resulting strain, designated BW30384(DE3)ΔompTΔmetEΔuxaC, was tested for loss of resistance to kanamycin, chloramphenicol and ampicillin (curing of pCP20), for the requirement of methionine (added at 0.1 mg/mL) during growth on Neidhardt minimal medium with glucose (4 mg/mL), and for the inability to grow on Neidhardt medium containing glucuronate as the carbon source (4 mg/mL) and methionine (0.1 mg/mL).

Example 22

Gene Expression in *E. coli* K-12 Methionine Auxotroph Hosts

The plasmid pCNAR ligation mix of Example 21 was transformed into the following electrocompetent *E. coli* K-12 strains: *E. coli* BW30384(DE3)ΔmetE(cat); *E. coli* BW30384(DE3)ΔompTΔmetE(cat); *E. coli* BW30384(DE3)ΔompTΔmetE; *E. coli* BW30384(DE3)ΔompTΔmetEΔuxaC (cat,kan); and *E. coli* BW30384(DE3)ΔompTΔmetEΔuxaC. The transformations were performed under standard conditions using a 0.1 cm cuvette and a Bio-Rad Gene Pulser II system as described in the Bio-Rad electroporation manual. The ligation mix was also transformed into Novagen *E. coli* B834(DE3) chemical competent cells following the manufacturer's directions. After recovery for one hour at 37° C. in SOC, the transformation mixes were plated on Neidhardt medium containing 0.4% glucose and supplemented with 2 mL/L Balch's vitamin solution. The plates were incubated at 37° C. for 36-48 h. Plasmid DNA was purified from liquid cultures of individual colonies using a QIAprep® Spin Miniprep Kit and screened by restriction digestion with XhoI/XbaI (for mio gene insert) and PsiI (for deletion of bla gene). In addition, the plasmid pCN(RR)-1 was transformed into *E. coli* BW30384(DE3)ΔmetE(cat) as described above. After recovery for one hour at 37° C. in SOC, the transformation mix was plated on LB+ampicillin (100 μg/mL) and incubated at 37° C. overnight. Plasmid DNA was purified from liquid cultures of individual colonies using a QIAprep® Spin Miniprep Kit and screened by restriction digestion with XhoI/XbaI to confirm the presence of the mio gene insert.

Gene Expression: Liquid cultures (5 mL) of Neidhardt medium containing 0.4% glucose and supplemented with 2 mL/L Balch's vitamin solution and 1.5 g/L Amino Acid Mix were inoculated from fresh plates or frozen glycerol stocks of the pCNAR-containing strains described above. Cultures were incubated at 37° C. at 230 rpm for 6-8 h. The OD600 of each culture was determined and the volume of culture necessary to obtain an OD600 of 0.05 in 25 mL was calculated. The calculated volumes of each liquid culture were transferred to flasks containing 25 mL of Novagen OVERNIGHT EXPRESS™ Autoinduction System 2 (a system that provides a complete, chemically defined medium for high-level protein expression with the pET system, and other IPTG-inducible expression systems, without the need to monitor growth) (Catalog #71366-3; solutions 1-5), and incubated at 30° C. with shaking at 230 rpm for 18 h. Cells were harvested by centrifugation and washed once with cold 50 mM MOPS, pH 7.0. Cells were then lysed using BUGBUSTER® (primary amine free) Extraction Reagent (Novagen Catalog #70923-3) containing 1 μL/mL benzonase nuclease (an endonuclease), 5 μL/mL Protease Inhibitor Cocktail Set II (Novagen) and 0.33 μL/10 mL r-Lysozyme (Novagen) following the Novagen recommended protocol. After incubation at 25° C. for 15 min with gentle shaking, the cell debris from each suspension was pelleted by centrifugation at 21,000 g for 15 min at 4° C. The supernatants (cell free extracts) were analyzed by SDS-PAGE on 4-15% gradient gels (Bio-Rad #161-1104) to detect soluble protein levels of the expressed myo-inositol oxygenase. The results indicated that MIO constituted about 40% of the total soluble protein for all strains.

Balch's vitamin solution (Balch, W. E., G. E. Fox, L. J. Magrum, C. R. Woese, and R. S. Wolfe. 1979. Microbiol. Rev. 43:260-296) components: p-Aminobenzoic Acid 5.0 mg, Folic Acid 2.0 mg, Biotin 2.0 mg, Nicotinic Acid 5.0 mg, Calcium pantothenate 5.0 mg, Riboflavin 5.0 mg, Thiamine HCl 5.0 mg, Pyridoxine HCl (vit B6) 10.0 mg, Cyanocobalamin (vit B12) 100.0 mg, Thioctic Acid (Lipoic acid) 5.0 mg. Adjust pH to 7.0 with 1M NaOH and the volume to 1 L with distilled water. Filter sterilize, store at 4° C. in the dark.

Amino Acid Mix:

Mix 1 g of each of the following amino acids together: Alanine, Arginine, Aspartic acid, Glutamic acid, Glycine, Histidine, Isoleucine, Leucine, Lysine, Phenylalanine, Proline, Serine, Threonine, Tryptophan, and Valine. Add 1.5 g of this solid mixture to 1 L of medium and sterilize. The final concentration of each amino acid is 100 mg/L of medium.

A number of embodiments of the invention have been described. Nevertheless, it will be understood that various modifications may be made without departing from the spirit and scope of the invention. Accordingly, other embodiments are within the scope of the following claims.

What is claimed is:

1. A method for producing D-glucuronic acid, comprising:
   incubating a mixture comprising myo-inositol, myo-inositol oxygenase, and oxygen; and
   maintaining a pH of the mixture between about 6.2 and about 8.5 during incubation, wherein D-glucuronic acid is formed by a reaction in a single reactor and at a final concentration ranging from about 5 grams D-glucuronic acid per liter of said mixture to about 400 grams D-glucuronic acid per liter of said mixture without removing D-glucuronic acid from the reactor during the reaction.

2. The method of claim 1, wherein said mixture further comprises a cell lysate, said cell lysate comprising said myo-inositol oxygenase.

3. The method of claim 1, wherein said myo-inositol is initially present at a concentration greater than about 20 grams per liter.

4. The method of claim 1, wherein said final concentration of D-glucuronic acid ranges from about 20 grams per liter to about 400 grams per liter.

5. The method of claim 1, wherein the final D-glucuronic acid concentration is greater than the final myo-inositol.

6. The method of claim 5, wherein the said final D-glucuronic acid concentration is at least twice the said final myo-inositol concentration.

7. The method of claim 1, wherein said mixture further comprises a buffer in a concentration ranging up to about 20 mM.

8. The method of claim 1, wherein said mixture further comprises Fe(II) in a concentration ranging up to about 40 mM.

9. The method of claim 1, said mixture further comprising at least one of a buffer in a concentration ranging up to about 20 mM, Fe(II) in a concentration ranging up to about 40 mM, or a reductant in a concentration ranging up to about 5 mM.

10. The method of claim 1, wherein said myo-inositol oxygenase is a *Cryptococcus neoformans* myo-inositol oxygenase.

11. The method of claim 1, wherein said oxygen is present during said incubation at a concentration ranging from about 10 µmol per liter of mixture to about 6500 µmol per liter of mixture.

12. The method of claim 11, wherein said oxygen is present at a concentration ranging from about 140 µmol to about 1550 µmol per liter of mixture.

13. The method of claim 1, further comprising the addition of a base during said incubating.

14. The method of claim 1, further comprising clarifying said mixture after said incubating step.

15. The method of claim 14, further comprising demineralizing said mixture after said clarifying step.

16. The method of claim 15, further comprising crystallizing said D-glucuronic acid formed in said incubating step.

17. The method of claim 1, further comprising forming glucurono-γ-lactone from said D-glucuronic acid formed in said incubating step.

18. The method of claim 17, wherein said forming glucurono-γ-lactone comprises heating said D-glucuronic acid at an acidic pH.

19. The method of claim 18, wherein said forming glucurono-γ-lactone comprises crystallizing glucurono-γ-lactone after said heating step.

20. The method of claim 1, wherein the mixture further comprises a reductant having a reduction potential of about −200 mV or greater at pH 7 in a concentration ranging from about 0.5 to about 500 mM.

21. The method of claim 20, wherein the mixture further comprises Fe(II) in a concentration ranging from about 0.2 to about 40 mM.

22. The method of claim 20, wherein said reductant is chosen from L-ascorbic acid and D-isoascorbic acid.

23. The method of claim 1, further comprising incubating the mixture in the presence of pure oxygen.

24. A method for producing D-glucuronic acid comprising:
   incubating a mixture comprising myo-inositol, myo-inositol oxygenase, and oxygen to form D-glucuronic acid, wherein D-glucuronic acid is formed by a reaction in a single reactor without removing D-glucuronic acid from the reactor during the reaction, and a final concentration of D-glucuronic acid is at least twice as great as a final concentration of myo-inositol.

25. The method of claim 24 further comprising: maintaining a pH level of the mixture between about 6.2 and about 7.6 during incubation.

26. The method of claim 25 wherein maintaining the pH level of the mixture includes adding sodium hydroxide to the mixture.

* * * * *